United States Patent
Hill et al.

(10) Patent No.: US 10,371,626 B2
(45) Date of Patent: Aug. 6, 2019

(54) SYSTEM AND METHOD FOR GENERATING MULTI-CHANNEL TUNABLE ILLUMINATION FROM A BROADBAND SOURCE

(71) Applicant: KLA-Tencor Corporation, Milpitas, CA (US)

(72) Inventors: Andrew V. Hill, Berkley, CA (US); Amnon Manassen, Haifa (IL); Ohad Bachar, Timrat (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/387,180

(22) Filed: Dec. 21, 2016

(65) Prior Publication Data

US 2018/0052099 A1 Feb. 22, 2018

Related U.S. Application Data

(60) Provisional application No. 62/375,996, filed on Aug. 17, 2016.

(51) Int. Cl.
*G01N 21/25* (2006.01)
*G01J 3/10* (2006.01)
(Continued)

(52) U.S. Cl.
CPC .............. *G01N 21/255* (2013.01); *G01J 3/10* (2013.01); *G01J 3/12* (2013.01); *G03F 7/70633* (2013.01);
(Continued)

(58) Field of Classification Search
CPC .... G01N 21/65; G01N 21/255; G01N 21/474; G01N 2201/0666; G01N 2201/0668;
(Continued)

(56) References Cited

U.S. PATENT DOCUMENTS

| 4,310,244 A | * | 1/1982 | Perkins | .................... G01J 3/18 356/334 |
| 2004/0145740 A1 | * | 7/2004 | Hopler | ..................... G01J 3/12 356/331 |

(Continued)

FOREIGN PATENT DOCUMENTS

| JP | 07083622 A | 3/1995 |
| JP | 2550651 B2 | 11/1996 |
| WO | 2009001390 A1 | 12/2008 |

*Primary Examiner* — Jamil Ahmed
(74) *Attorney, Agent, or Firm* — Suiter Swantz pc llo

(57) ABSTRACT

A metrology system includes an illumination source to generate an illumination beam, a multi-channel spectral filter, a focusing element to direct illumination from the single optical column to a sample, and at least one detector to capture the illumination collected from the sample. The multi-channel spectral filter includes two or more filtering channels having two or more channel beam paths. The two or more filtering channels filter illumination propagating along the two or more channel beam paths based on two or more spectral transmissivity distributions. The multi-channel spectral filter further includes a channel selector to direct at least a portion of the illumination beam into at least one selected filtering channel to filter the illumination beam. The multi-channel spectral filter further includes at least one beam combiner to combine illumination from the two or more filtering channels to a single optical column.

50 Claims, 13 Drawing Sheets

(51) Int. Cl.
*G01J 3/12* (2006.01)
*G03F 7/20* (2006.01)

(52) U.S. Cl.
CPC .......... *G01J 2003/1213* (2013.01); *G01N 2201/0666* (2013.01); *G01N 2201/0668* (2013.01); *G01N 2201/0675* (2013.01); *G01N 2201/0683* (2013.01)

(58) Field of Classification Search
CPC .... G01N 2201/0675; G01N 2201/0683; G01J 3/10; G01J 3/12; G01J 3/18; G01J 2003/1213; G01J 4/00; G01B 9/02; G01B 9/02004; F21V 13/08; G06K 9/00
See application file for complete search history.

(56) References Cited

U.S. PATENT DOCUMENTS

| | | | |
|---|---|---|---|
| 2006/0065823 A1* | 3/2006 | Schreiber | G02B 21/008 250/234 |
| 2008/0175465 A1* | 7/2008 | Jiang | G01B 9/02004 382/131 |
| 2009/0262366 A1 | 10/2009 | Den Boef | |
| 2010/0301232 A1 | 12/2010 | Erlbacher et al. | |
| 2011/0310388 A1* | 12/2011 | Hill | G01N 21/474 356/369 |
| 2014/0240951 A1* | 8/2014 | Brady | F21V 13/08 362/19 |
| 2015/0369742 A1* | 12/2015 | Tamada | G01N 21/65 356/301 |
| 2017/0373463 A1* | 12/2017 | Narumi | H01S 3/137 |

* cited by examiner

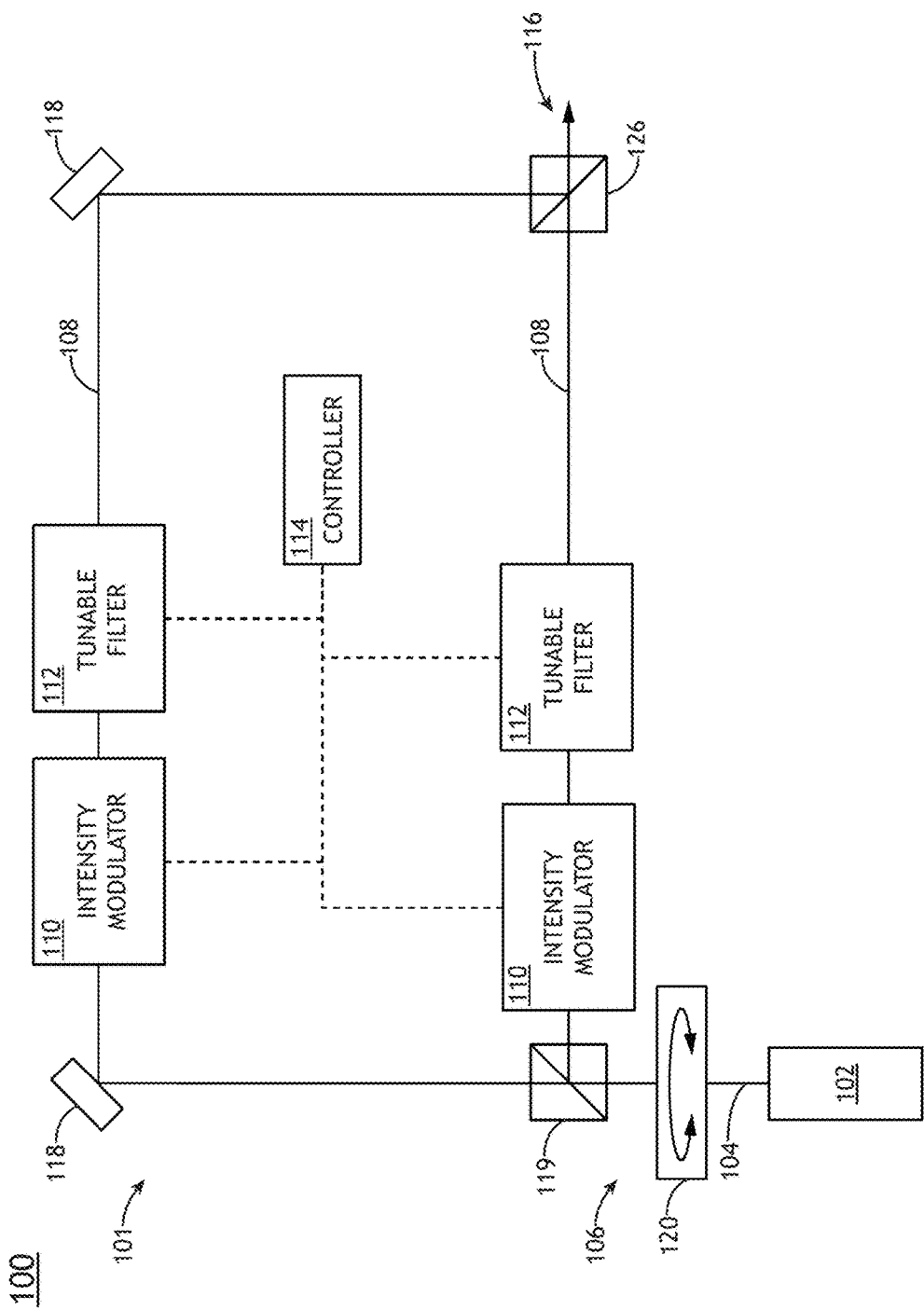

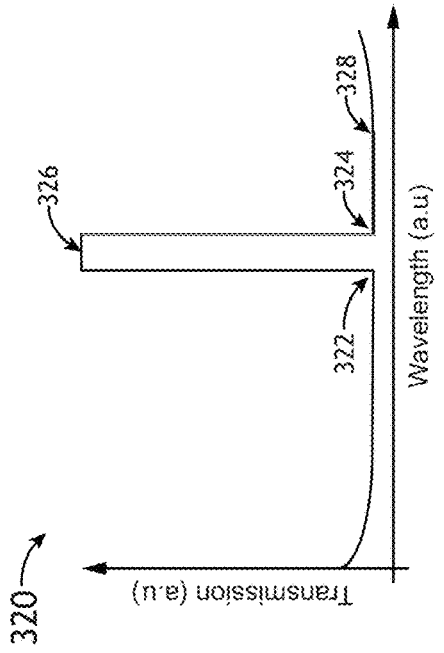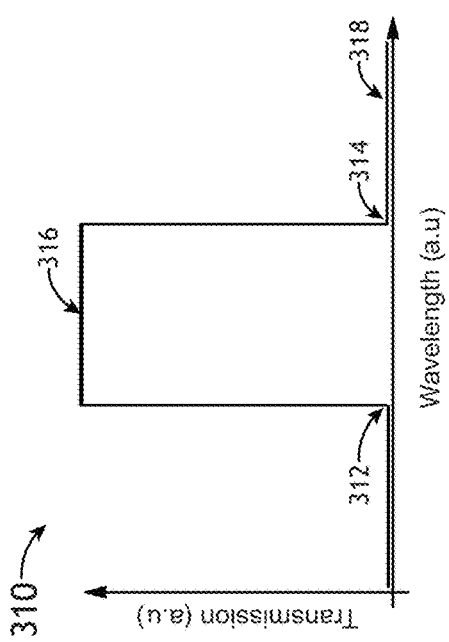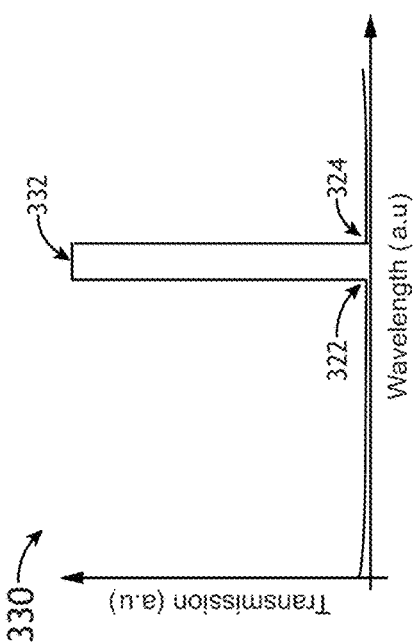
FIG. 3B
FIG. 3C
FIG. 3D

SYSTEM AND METHOD FOR GENERATING MULTI-CHANNEL TUNABLE ILLUMINATION FROM A BROADBAND SOURCE

CROSS-REFERENCE TO RELATED APPLICATION

The present application claims the benefit under 35 U.S.C. § 119(e) of U.S. Provisional Application Ser. No. 62/375,996, filed Aug. 17, 2016, entitled SYSTEM AND METHOD FOR GENERATING MULTI-CHANNEL TUNABLE ILLUMINATION FROM A BROADBAND SOURCE, naming Andrew V. Hill, Amnon Manassen, and Ohad Bachar as inventors, which is incorporated herein by reference in the entirety.

TECHNICAL FIELD

The present disclosure relates generally to broadband illumination sources, and, more particularly, to generating multiple illumination spectra from a single broadband illumination source.

BACKGROUND

Tunable light sources may provide illumination tuned to one or more select wavelengths within a given spectral range. However, typical tunable light sources may suffer from a limited capacity to independently and precisely modify the total intensity, spectral power, and/or polarization of multiple spectral regions of a tuned illumination beam. Therefore, it would be desirable to provide a system and method for curing defects such as those of the identified above.

SUMMARY

A metrology system is disclosed, in accordance with one or more illustrative embodiments of the present disclosure. In one illustrative embodiment, the system includes an illumination source to generate an illumination beam. In another illustrative embodiment, the system includes a multi-channel spectral filter. In another illustrative embodiment, the multi-channel spectral filter includes two or more filtering channels including two or more channel beam paths. In another illustrative embodiment, the two or more filtering channels filter illumination propagating along the two or more channel beam paths based on two or more spectral transmissivity distributions. In another illustrative embodiment, the multi-channel spectral filter includes a channel selector to direct at least a portion of the illumination beam into at least one selected filtering channel of the two or more filtering channels to filter the at least a portion of the illumination beam based on a selected spectral transmissivity distribution of the two or more spectral transmissivity distributions. In another illustrative embodiment, the multi-channel spectral filter includes at least one beam combiner to combine illumination from the two or more filtering channels to a single optical column. In another illustrative embodiment, the system includes a focusing element to direct illumination from the single optical column to a sample. In another illustrative embodiment, the system includes at least one detector to capture radiation from the sample.

A multi-channel spectral filter is disclosed, in accordance with one or more illustrative embodiments of the present disclosure. In one illustrative embodiment, the multi-channel spectral filter includes two or more filtering channels including two or more channel beam paths. In another illustrative embodiment, the two or more filtering channels filter illumination propagating along the two or more channel beam paths based on two or more spectral transmissivity distributions. In another illustrative embodiment, the multi-channel spectral filter includes a channel selector to direct at least a portion of an illumination beam into at least one selected filtering channel of the two or more filtering channels to filter the at least a portion of the illumination beam based on a selected spectral transmissivity distribution of the two or more spectral transmissivity distributions.

A multi-channel illumination source is disclosed, in accordance with one or more illustrative embodiments of the present disclosure. In one illustrative embodiment, the multi-channel illumination source includes a broadband illumination source configured to generate an illumination beam. In another illustrative embodiment, the multi-channel illumination source includes a multi-channel spectral filter. In another illustrative embodiment, the multi-channel spectral filter includes two or more filtering channels including two or more channel beam paths. In another illustrative embodiment, the two or more filtering channels filter illumination propagating along the two or more channel beam paths based on two or more spectral transmissivity distributions. In another illustrative embodiment, the multi-channel spectral filter includes a channel selector configured to direct at least a portion of the illumination beam into at least one selected filtering channel of the two or more filtering channels to filter the at least a portion of the illumination beam based on a selected spectral transmissivity distribution of the two or more spectral transmissivity distributions.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which:

FIG. 1C is a conceptual view of a multi-channel tunable spectral filter having two channel beams in which the two channels are combined into a combined output illumination beam, in accordance with one or more embodiments of the present disclosure.

FIG. 3B is a diagram illustrating the spectral transmissivity of a first spectral filter, in accordance with one or more embodiments of the present disclosure.

FIG. 3C is a diagram illustrating the spectral transmissivity of a second spectral filter, in accordance with one or more embodiments of the present disclosure.

FIG. 3D is a diagram illustrating the spectral transmissivity of the first spectral filter of FIG. 3B cascaded with the second spectral filter of FIG. 3C, in accordance with one or more embodiments of the present disclosure.

DETAILED DESCRIPTION

Figure 1A:
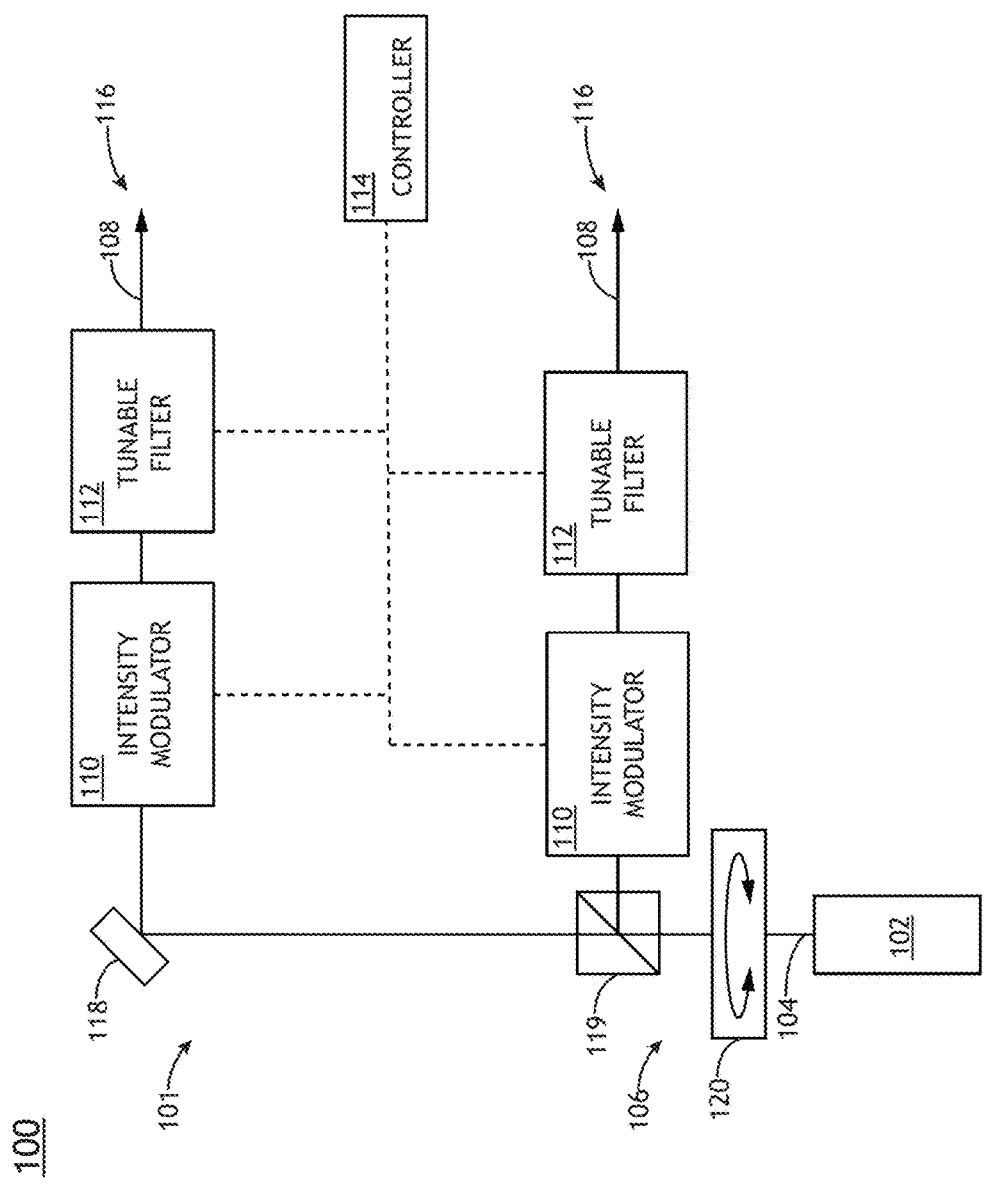
FIG. 1A is a conceptual view of a multi-channel illumination source including a multi-channel tunable spectral filter and a broadband illumination source having a broad spectrum, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Referring generally to FIGS. 1 through 9, systems and methods for tuning the spectral distribution of a broadband illumination source are disclosed, in accordance with one or more embodiments of the present disclosure. Embodiments of the present disclosure are directed to a multi-channel tunable spectral filter. For example, a multi-channel tunable spectral filter may separate an input illumination beam into one or more channels such that each channel beam may have an independently modifiable spectral distribution, total intensity, and/or polarization. In this regard, a multi-channel tunable spectral filter may tune the spectrum of an incident beam of illumination by directing portions of the illumination beam through one or more filtering channels. Additional embodiments are directed to a multi-channel tunable filter in which channel beams (e.g. portions of the incident illumination beam propagating along the filtering channels) are provided as output illumination beams. Additional embodiments are directed to a multi-channel tunable filter in which two or more channel beams are combined to form a combined output illumination beam. Additional embodiments are directed to a multi-channel illumination source including a broadband illumination source and a multi-channel tunable spectral filter. Further embodiments are directed to a metrology system including a multi-channel illumination source.

A typical spectral filter may modify the spectrum of incident illumination (e.g. electromagnetic radiation, or the like) by reducing the spectral power of select wavelengths relative to others. Accordingly, a spectral transmittance of a spectral filter may describe the transmittance (e.g. from 0% to 100%, 0 to 1, or the like) of illumination as a function of wavelength. It is noted that transmittance may refer to illumination passed by the filter through transmission and/or reflection. For example, a typical spectral filter may include, but is not limited to, one or more wavelength-dependent filters, one or more spectral filters or one or more spatial filters located in a lens Fourier plane in which the spectral content is spatially distributed.

A tunable spectral filter may selectively modify the spatial transmittance as a function of wavelength such that the spectrum of incident illumination may be dynamically tuned. In this regard, a tunable spectral filter may selectively modify the spectral power (e.g. the power per unit wavelength) of illumination. For example, a tunable spectral filter may modify the spectral transmittance by a variety of methods such as, but not limited to, replacing a spectral filter having a fixed spectral transmissivity with another (e.g. via a filter changer, or the like), adjusting the position and/or angle of a spectral filter having an orientation-dependent spectral transmissivity, or translating one or more spatial filtering elements.

It is recognized herein that a tuning speed at which the spectral transmissivity of a tunable spectral filter may be modified may be highly dependent on the components of the tunable filter. In many cases, the switching speed may be dependent on the speed at which one or more elements may be physically translated. Some embodiments of the present disclosure are directed to a multi-channel tunable spectral filter having multiple spectral filtering channels and a channel selector. The spectral filtering channels may have differing spectral transmissivities that may be generated based on any spectral filtering technique known in the art. In this regard, a spectrum of an incident illumination beam may be tuned by dynamically selecting which filtering channel or channels portions of the illumination beam propagate through. Accordingly, a switching speed at which a channel selector may selectively direct portions of the illumination beam between channels may be faster than a tuning speed of a single tunable spectral filter.

A multi-channel tunable spectral filter described in accordance with embodiments of the present disclosure may provide one or more channel beams having different spectral content. In one embodiment, each filtering channel provides a separate channel beam as an output beam from the multi-channel tunable spectral filter. In another embodiment, the channel beams from multiple spectral channels are combined into a combined output beam. For example, a single-output multi-channel tunable spectral filter having multiple filtering channels with different spectral transmissivities may, but is not required to, dynamically tune the spectrum of an illumination beam by selectively switching the full power of the illumination beam between the multiple filtering channels.

Additional embodiments of the present disclosure are directed to a multi-channel tunable spectral filter in which the spectral transmissivity of the filtering channels may be tuned. For example, a channel including a tunable band-pass filter may, but is not required to, dynamically modify the central wavelength of passed illumination, a low-pass cutoff wavelength, a high-pass cutoff wavelength, a spectral bandwidth, a sharpness of a transition between passed wavelengths and filtered wavelengths, or the like. It is noted that the switching time associated with distributing illumination between filtering channels may be faster than the tuning time of a filtering channel. However, a multi-channel tunable spectral filter with independently tunable filtering channels may provide a flexible platform for rapid switching between different spectral transmissivities. For example, in one embodiment, a multi-channel tunable spectral filter may direct illumination from an illumination beam through one or more filtering channels while simultaneously modifying the spectral transmissivity of one or more additional tuning channels. Accordingly, the multi-channel tunable spectral filter may subsequently direct illumination from the illumination beam to the one or more additional filtering channels without a time delay associated with tuning a particular filtering channel. In a general sense, a multi-channel tunable spectral filter may enable rapid tuning of the spectrum of an incident illumination beam using any spectral tuning method within each channel (e.g. fixed spectral transmissivity in filtering channels, relatively slowly tunable spectral transmissivity of filtering channels, or the like).

Additionally, each channel of a multi-channel tunable spectral filter may provide, but is not required to provide, rapid modification of the spectral content of filtered illumination, a stable spectrum of filtered illumination, minimal loss of spectral power within a desired spectral range for passed illumination, maximal attenuation of spectral power within an undesired spectral range for rejected illumination, a sharp transition between passed wavelengths and rejected wavelengths of illumination, a high tunable spectral resolution (e.g. an ability to selectively modify the spectral power of a narrow wavelength range, or the like), and/or a minimal perturbation of the phase distribution of the filtered illumination.

In the context of illumination sources for metrology systems, a multi-channel illumination source including a multi-channel tunable spectral filter may provide one or more beams of illumination with independently tuned spectral content (e.g. with a tunable spectral bandwidth of illumination, the central wavelength of the pass-band, or the like) to be directed to a sample. In this regard, a metrology system including a multi-channel illumination source with independent spectral control for each channel may illuminate a sample with selectively controlled spectra over a broad continuous range of wavelengths. Additionally, the multi-channel illumination source may illuminate the sample with illumination from each channel simultaneously or sequentially. Further, the multi-channel illumination source may illuminate different portions of a sample (e.g. different cells of a metrology target, or the like) with different channels of illumination. In this regard, a multi-channel illumination source may enable optimization of multiple illumination profiles (e.g. multiple spectral profiles) for different cells of a metrology target.

An angularly resolved scatterometer is generally described in U.S. Patent Application Publication No. 2009/0262366, published on Oct. 22, 2009, which is incorporated herein by reference in its entirety. Additionally, it is noted that multi-channel spectrally tunable illumination source may be beneficially utilized in a wide range of applications. Accordingly, the spirit and scope of the present disclosure may extend to any application of a multi-channel spectrally tunable illumination source.

FIG. 1A is a conceptual view of a multi-channel illumination source 100 including a multi-channel tunable spectral filter 101 and a broadband illumination source 102 having a broad spectrum (e.g. a range of wavelengths of illumination), in accordance with one or more embodiments of the present disclosure. In one embodiment, the broadband illumination source 102 generates an illumination beam 104. The broadband illumination source 102 may include any type of illumination source suitable for providing an illumination beam 104 having a large range of wavelengths. In one embodiment, the broadband illumination source 102 is a laser source. For example, the broadband illumination source 102 may include, but is not limited to, a broadband laser source, a supercontinuum laser source, a white light laser source, or the like. In this regard, the broadband illumination source 102 may provide an illumination beam 104 having high coherence (e.g. high spatial coherence and/or temporal coherence). In another embodiment, the broadband illumination source 102 includes a laser-sustained plasma (LSP) source. For example, the broadband illumination source 102 may include, but is not limited to, a LSP lamp, a LSP bulb, or a LSP chamber suitable for containing one or more elements that, when excited by a laser source into a plasma state, may emit broadband illumination. In another embodiment, the broadband illumination source 102 includes a lamp source. For example, the broadband illumination source 102 may include, but is not limited to, an arc lamp, a discharge lamp, an electrode-less lamp, or the like. In this regard, the broadband illumination source 102 may provide an illumination beam 104 having low coherence (e.g. low spatial coherence and/or temporal coherence).

The broadband illumination source 102 may further produce broadband illumination with any temporal profile. For example, the broadband illumination source 102 may produce a continuous illumination beam 104, a pulsed illumination beam 104, or a modulated illumination beam 104. Additionally, the illumination beam 104 may be delivered from the broadband illumination source 102 via free-space propagation or guided light (e.g. an optical fiber, a light pipe, or the like).

In another embodiment, a multi-channel tunable spectral filter 101 includes a channel selector 106 to separate the illumination beam 104 into two or more channel beams 108 (e.g. portions of the illumination beam propagating along any of the two or more filtering channels. In another embodiment, one or more channels of the multi-channel tunable spectral filter 101 include an intensity modulator 110 to control the intensity of the channel beam 108. In another embodiment, one or more channels of the multi-channel tunable spectral filter 101 include a tunable filter 112 to control the spectral content of the channel beam 108. In another embodiment, the multi-channel tunable spectral filter 101 includes a controller 114 communicatively coupled to at least one of the intensity modulator 110 or the tunable filter 112. In this regard, the controller 114 may provide one or more signals to one or more components of the intensity modulator 110 and/or the tunable filter 112 to tune the intensity and/or spectral content of each of the channel beams 108. In another embodiment, each of the channel beams 108 are provided as output illumination beams 116. Accordingly, output illumination beams 116 may be provided to an external system (e.g. an illumination source, a metrology system, or the like).

In another embodiment, the controller 114 includes one or more processors 128. In another embodiment, the one or more processors 128 are configured to execute a set of program instructions maintained in a memory medium 130, or memory. Further, the controller 114 may include one or more modules containing one or more program instructions stored in the memory medium 130 executable by the one or more processors 128. The one or more processors 128 of a controller 114 may include any processing element known in the art. In this sense, the one or more processors 128 may include any microprocessor-type device configured to execute algorithms and/or instructions. In one embodiment, the one or more processors 128 may consist of a desktop computer, mainframe computer system, workstation, image computer, parallel processor, or any other computer system (e.g., networked computer) configured to execute a program configured to operate the multi-channel tunable spectral filter 101, as described throughout the present disclosure. It is further recognized that the term "processor" may be broadly defined to encompass any device having one or more processing elements, which execute program instructions from a non-transitory memory medium 130.

It is recognized herein that the steps described throughout the present disclosure may be carried out by the controller 114. Further, the controller 114 may be formed from a single component or multiple components. It is further noted herein that the multiple components of the controller 114 may be housed in a common housing or within multiple housings. In this way, any controller or combination of controllers may be separately packaged as a module suitable for integration into the multi-channel tunable spectral filter 101.

The memory medium 130 may include any storage medium known in the art suitable for storing program instructions executable by the associated one or more processors 128. For example, the memory medium 130 may include a non-transitory memory medium. As an additional example, the memory medium 130 may include, but is not limited to, a read-only memory, a random access memory, a magnetic or optical memory device (e.g., disk), a magnetic tape, a solid state drive and the like. It is further noted that memory medium 130 may be housed in a common controller housing with the one or more processors 128. In one embodiment, the memory medium 130 may be located remotely with respect to the physical location of the one or more processors 128 and controller 114. For instance, the one or more processors 128 of controller 114 may access a remote memory (e.g., server), accessible through a network (e.g., internet, intranet and the like). Therefore, the above description should not be interpreted as a limitation on the present invention but merely an illustration.

In another embodiment, the multi-channel tunable spectral filter 101 includes one or more steering mirrors 118 to direct the paths of the channel beams 108a,b.

The channel selector 106 may be any optical element or set of optical elements suitable for directing the illumination beam 104 into two or more channel beams 108. For example, the channel selector 106 may include one or more beamsplitters 119. By way of another example, the channel selector 106 may include one or more dichroic mirrors. In one embodiment, the channel selector 106 separates the illumination beam 104 such that generated channel beams 108 have the same spectra. For instance, the channel selector 106 may include one or more beamsplitters (e.g. beamsplitters 119, or the like) to separate the illumination beam 104 without modifying the spectral content of the illumination beam 104. In another embodiment, the channel selector 106 may separate the illumination beam 104 such that the generated channel beams 108 may have distinct spectra. For example, the channel selector 106 may include one or more dichroic mirrors to selectively reflect a first portion of the illumination beam 104 to generate a first channel beam 108 having a first spectrum and transmit a second portion of the illumination beam 104 to generate a second channel beam 108 having a second spectrum. Further, the channel selector 106 may include polarization-sensitive optical elements and/or polarization insensitive elements.

In another embodiment, the channel selector 106 may include a series of two or more beam separating elements (e.g. beamsplitters, dichroic mirrors, or the like) to generate three or more channel beams 108. For example, a channel selector 106 configured to generate four channel beams may include three cascaded beam separating elements such that a first beam separating element may separate the illumination beam 104 into a first channel beam and a first intermediate beam, a second beam separating element may separate the first intermediate beam into a second channel beam and a second intermediate beam, and the third beam separating element may separate the second intermediate beam into a third channel beam and a fourth channel beam. In a general sense, a channel selector 106 may generate any number of channel beams 108.

In another embodiment, the channel selector 106 includes one or more routing elements to selectively direct the illumination beam into one of multiple available channels. In this regard, each channel may be configured to provide a unique spectral distribution (e.g. via a unique configuration of a tunable filter 112, or the like). Accordingly, the one or more routing elements may control the channel the illumination beam 104 is directed to and thus provide rapid switching of the spectral distribution of the output illumination beam 116. The one or more routing elements may include any optical and/or mechanical elements suitable for directing an illumination beam 104 such as, but not limited to, an acousto-optic modulator, an electro-optic modulator, a galvanometer mirror, or a piezo-electric mirror.

Further, the intensity of the illumination beam 104 may be divided between the channel beams 108 according to any ratio. In one embodiment, each of the channel beams 108 exhibits the same intensity. For example, the channel selector 106 may include a beamsplitter having a 50/50 intensity ratio to generate two channel beams 108 having the same intensity. By way of another example, the channel selector 106 may include a first beamsplitter to generate a first channel beam 108 having one third of the intensity of the illumination beam 104 and two thirds of the intensity of the illumination beam 104 in an intermediate beam. Further the channel selector 106 may include a second beamsplitter having a 50/50 intensity ratio to split the intermediate beam into a second channel beam 108 and a third channel beam 108 such that the three channel beams 108 each have one third of the intensity of the illumination beam 104. In another embodiment, each of the channel beams 108 exhibits a different intensity.

In another embodiment, the multi-channel tunable spectral filter 101 includes polarization-controlling optical elements. For example, the multi-channel tunable spectral filter 101 may include, but is not required to include, one or more polarizers, one or more waveplates, or one or more electro-optic cells (e.g. Pockels cells, or the like). For example, as illustrated in FIG. 1A, the channel selector 106 may include a polarization rotator 120 (e.g. a waveplate, an electro-optical cell, or the like) in the path of the illumination beam 104. Further, the channel selector 106 may include one or more polarized beamsplitters (e.g. beamsplitters 119, or the like). In this regard, different channel beams 108 may be associated with different polarizations and the relative intensity of the channel beams 108 may be controllable by adjusting the polarization angle of the illumination beam 104 with the polarization rotator 120 with respect to the orientation of the polarized beam splitter.

In one instance, one or more channels of the multi-channel tunable spectral filter 101 may include a polarization rotator to adjust the polarization of a channel beam 108. By way of another example, the multi-channel tunable spectral filter 101 may include one or more polarization-based intensity modulators. For example, a polarization-based intensity modulator may include a polarization controller and a polarizer. In this regard, the multi-channel tunable spectral filter 101 may include polarization-controlling elements in any beam path to selectively control the polarization of any beam such as, but not limited to, the illumination beam 104 from the broadband illumination source 102, any channel beam 108, or any output illumination beam 116.

For example, polarization-sensitive optical elements may be mounted in rotatable mounts such that the orientations of the polarization-sensitive optical elements may be selectively controllable (e.g. via control signals from the controller 114, through manual adjustment by a user, or the like).

The output illumination beams 116 may be provided by the multi-channel tunable spectral filter 101 by any method known in the art. In one embodiment, one or more output illumination beams 116 are provided as a free-space illumination beam. In another embodiment, one or more output illumination beams 116 are fiber-coupled. For example, one or more output illumination beams 116 may be coupled to a single-mode fiber. In one instance, spatially coherent output illumination beams 116 (e.g. provided by a spatially-coherent broadband illumination source 102) may be coupled to a single-mode fiber. By way of another example, one or more output illumination beams 116 may be coupled to a multi-mode fiber. In another instance, spatially-incoherent output illumination beams 116 (e.g. from a spatially incoherent broadband illumination source 102, a speckle-busted spatially coherent broadband illumination source 102, or the like) may be coupled into a multi-mode fiber.

Figure 1B:
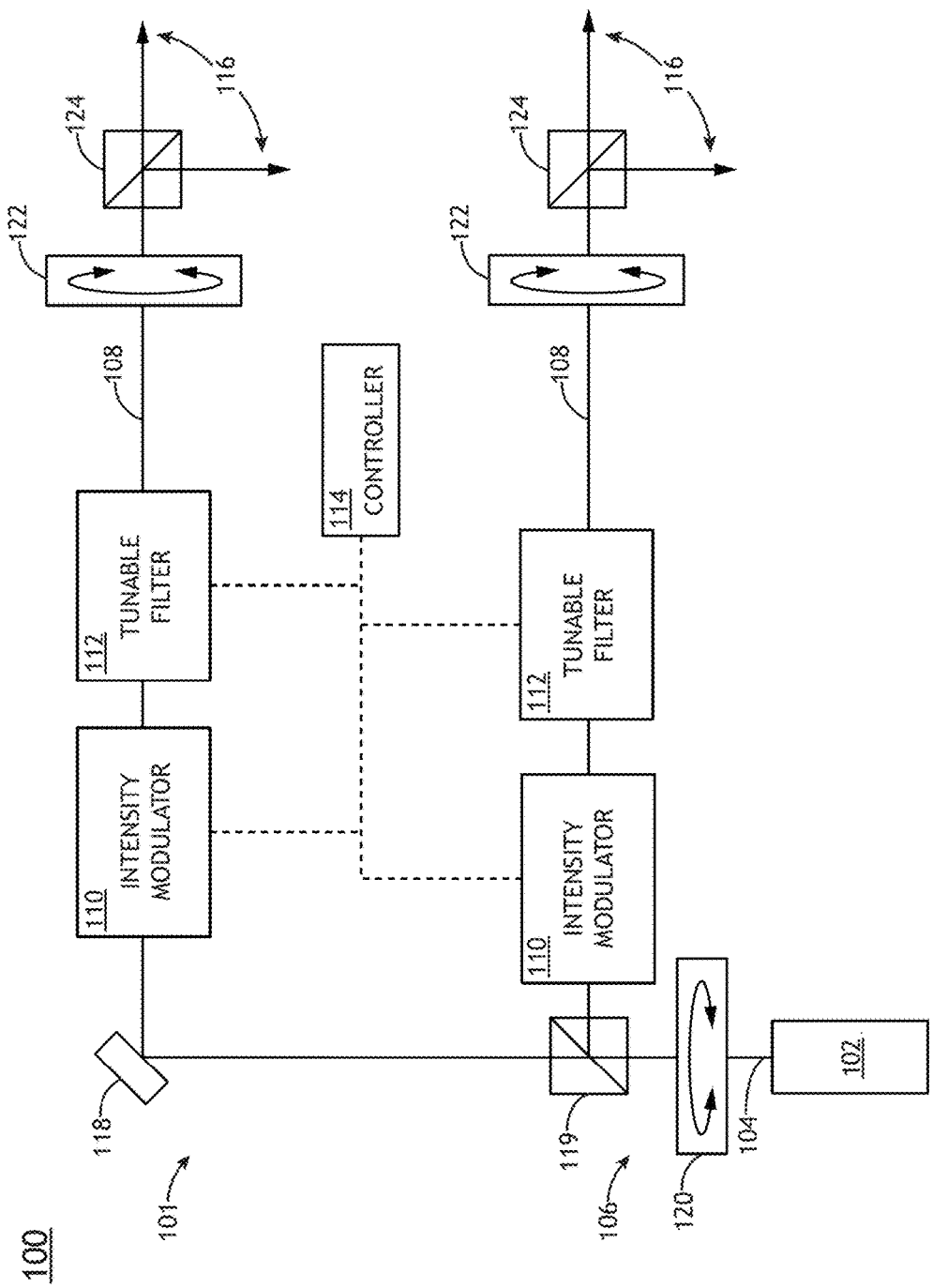
FIG. 1B is a conceptual view of a multi-channel tunable spectral filter in which channel beams are further split into multiple output illumination beams, in accordance with one or more embodiments of the present disclosure.

FIG. 1B is a conceptual view of a multi-channel tunable spectral filter 101 in which channel beams 108 are further split into multiple output illumination beams 116, in accordance with one or more embodiments of the present disclosure. In one embodiment, the multi-channel tunable spectral filter 101 includes an output polarization rotator 122 and an output beam separator 124 for each channel beam 108. In this regard, each channel beam 108 may be further split into multiple output illumination beams 116 having independently-adjustable intensity. Further, each output illumination beam 116 may be independently provided to an external system (e.g. to illuminate multiple locations of a sample, or the like). In another embodiment, a multi-channel tunable spectral filter 101 includes an adjustable polarizer (not shown) in the beam path of one or more channel beams 108 to selectively adjust the polarization of a channel beam 108. For example, an adjustable polarizer may be placed prior to a polarizing beamsplitter to selectively control the intensity ratio of output illumination beams 116.

The multi-channel tunable spectral filter 101 may provide any channel as an output illumination beam 116. Further, two or more channels of the multi-channel tunable spectral filter 101 may be combined into a single output illumination beam 116. FIG. 1C is a conceptual view of a multi-channel tunable spectral filter 101 having two channel beams 108a,b in which the two channels are combined into a combined output illumination beam 116, in accordance with one or more embodiments of the present disclosure. In one embodiment, the multi-channel tunable spectral filter 101 includes a beam combiner 126 to combine the two channel beams 108a,b. The beam combiner 126 may be any optical element or set of optical elements suitable for combining the channel beams 108a,b into a combined output illumination beam 116. For example, the channel selector 106 may include, but is not limited to, one or more beamsplitters or one or more dichroic mirrors. Further, the beam combiner 126 may include polarizing and/or non-polarizing optical elements. In another embodiment, the channel selector 106 and the beam combiner 126 are formed from non-polarized beam splitters. Accordingly, the channel beams 108a,b may have the same polarization. In another embodiment, the channel selector 106 and the beam combiner 126 include polarized beamsplitters. In this regard, the channel selector 106 may separate the illumination beam 104 into two orthogonally-polarized channel beams 108a,b. Further, the beam combiner 126 may combine the orthogonally-polarized channel beams 108a,b into a single output illumination beam 116.

Figure 1D:
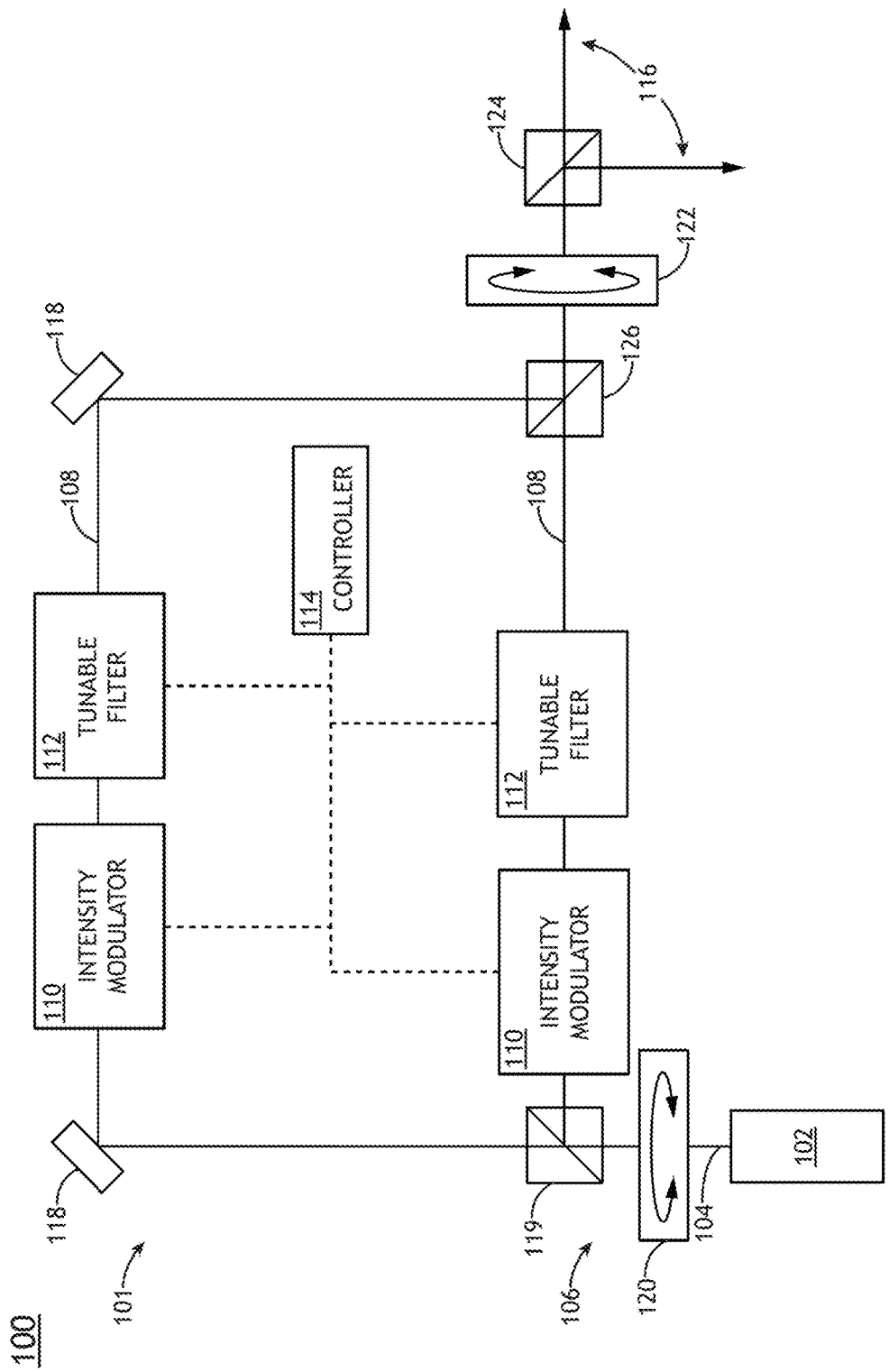
FIG. 1D is a conceptual view of a multi-channel tunable spectral filter in which a combined output illumination beam is further split into multiple output illumination beams, in accordance with one or more embodiments of the present disclosure.

FIG. 1D is a conceptual view of a multi-channel tunable spectral filter 101 in which a combined output illumination beam 116 is further split into multiple output illumination beams 116, in accordance with one or more embodiments of the present disclosure. In one embodiment, the multi-channel tunable spectral filter 101 includes an output polarization rotator 122 and an output beam separator 124 in the beam path of a combined output illumination beam 116. In this regard, the combined output illumination beam 116 may be further split into multiple output illumination beams 116 having independently-adjustable intensity. Further, each output illumination beam 116 may be independently provided to an external system (e.g. to simultaneously illuminate multiple locations of a sample, or the like).

Figure 2:
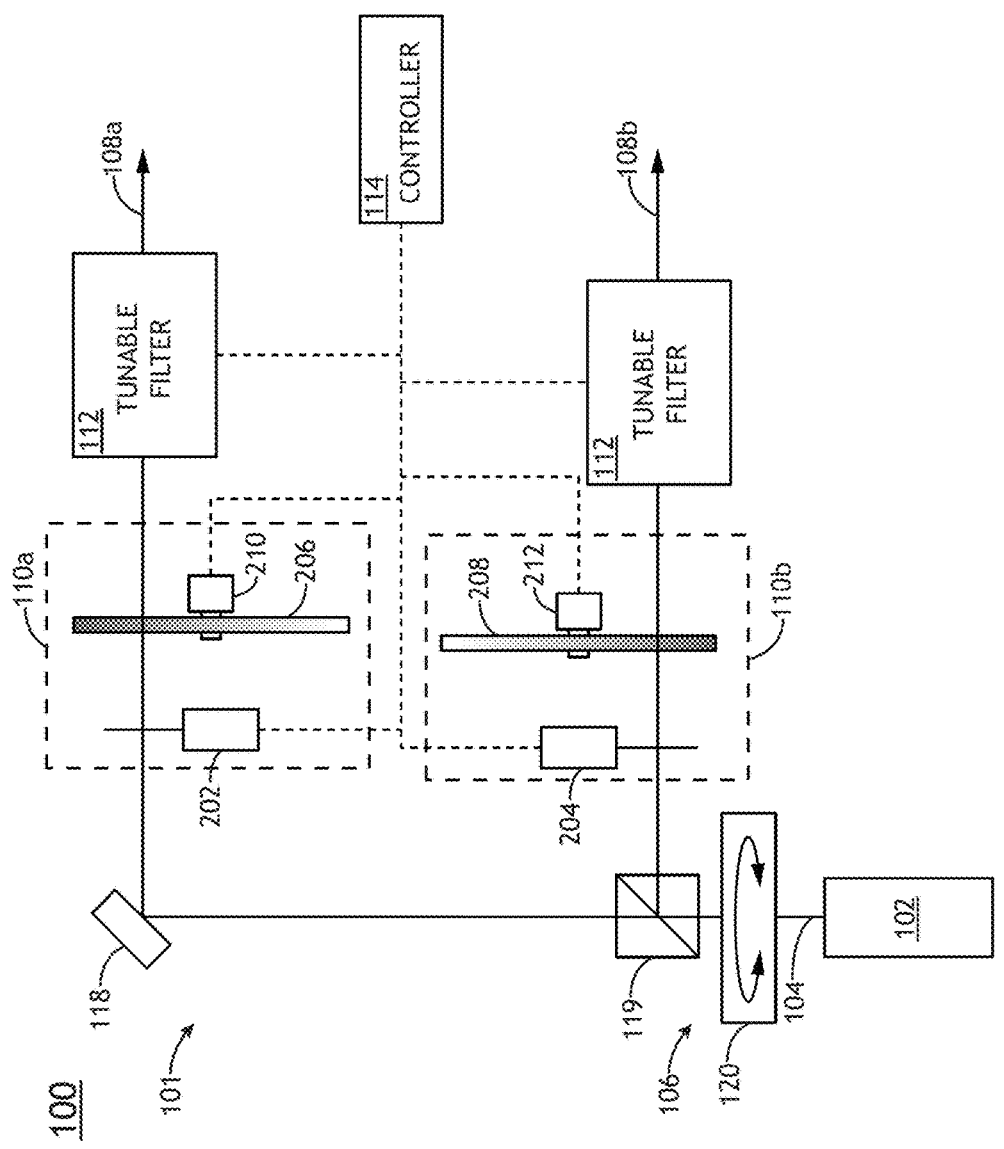
FIG. 2 is a conceptual view of a multi-channel illumination source illustrating an expanded view of an intensity modulator, in accordance with one or more embodiments of the present disclosure.

FIG. 2 is a conceptual view of a multi-channel tunable spectral filter 101 illustrating an expanded view of an intensity modulator 110, in accordance with one or more embodiments of the present disclosure. An intensity modulator 110 may include any optical element or combination of optical elements suitable for modifying the intensity of one or more channel beams 108.

An intensity modulator 110 in the path of a channel beam 108 may include a shutter to selectively block one or more channel beams 108. In one embodiment, as illustrated in FIG. 2, a first intensity modulator 110a includes a first shutter 202 to selectively block a first channel beam 108a. In another embodiment, a second intensity modulator 110b includes a second shutter 204 to selectively block a second channel beam 108b. Further, a shutter may include any type of shutter known in the art for selectively blocking a channel beam including, but not limited to, a mechanical shutter, an acousto-optic shutter, or an electro-optic shutter. In another embodiment, a shutter may be communicatively coupled with the controller 114. In this regard, the controller 114 may selectively actuate the shutter to pass or block a channel beam (e.g. channel beam 108a,b).

An intensity modulator 110 in the path of a channel beam 108 may include an intensity filter. In one embodiment, as illustrated in FIG. 2, the first intensity modulator 110a includes a first intensity filter 206*a*. In another embodiment, the second intensity modulator 110*b* includes a second intensity filter 208. Further, an intensity filter may include any type of optical element or set of optical elements suitable for selectively attenuating the spectral power of one or wavelengths of a channel beam 108. In one embodiment, an intensity filter may include one or more neutral density filters to attenuate the intensity of all wavelengths of a channel beam 108 by the same degree. In another embodiment, an intensity filter includes an adjustable neutral density filter. Further, the intensity filter may be communicatively coupled with the controller 114. In this regard, the controller 114 may selectively control the intensity of each channel beam 108. For example, the intensity filter may include one or more filter changers (e.g. filter wheels, or the like) having a set of neutral density filters. For instance, a filter changer may include two or more filter mounts arranged such that filters secured to the filter mounts may be selectively placed in the path of a channel beam 108. In this regard, the intensity of a channel beam 108 may be adjusted by selectively controlling the number and optical density of the neutral density filters placed in the path of the channel beam 108. By way of another example, the intensity filter may include a gradient filter in which the transmissivity (or reflectivity) of the intensity filter may vary in a gradient pattern as a function of position on the intensity filter. In one instance, the intensity filter may include a linear gradient filter mounted to a linearly actuatable translation stage (e.g. coupled to the controller 114) such that the intensity of a channel beam 108 may be controllable by actuating the linear position of the linear gradient filter with respect to the channel beam 108. In another instance, the intensity filter includes a polarization controller and a polarizer. In a further instance, as illustrated in FIG. 2, the intensity filter may be a circular gradient filter mounted to a rotational stage (e.g. rotational stage 210 or rotational stage 212) in which the transmissivity (or reflectivity) of the intensity filter may be controllable by actuating the rotational position of the intensity filter with respect to the channel beam 108.

In another embodiment, the multi-channel tunable spectral filter 101 may include an intensity modulator in the beam path of any output illumination beam 116 (e.g. output illumination beams 116 illustrated in FIG. 1B, FIG. 1D, or the like). In this regard, the intensity of any output illumination beam 116 may be selectively adjusted from completely blocked to fully transmitted.

Referring generally to FIGS. 3A through 7, a tunable filter 112 may include any optical element or combination of optical elements suitable for modifying the spectral content of one or more channel beams 108. In one embodiment, the tunable filter 112 includes a spectral filter to selectively attenuate one or more wavelengths of a channel beam 108. For example, the tunable filter 112 may include a low-pass filter to attenuate wavelengths above a cutoff wavelength, a high-pass filter to attenuate wavelengths below a cutoff wavelength, a band-pass filter to pass a defined spectral bandwidth of illumination and attenuate wavelengths outside of a select band of wavelengths, a band-reject filter to attenuate wavelengths within a select band of wavelengths, or the like. The tunable filter 112 may include any type of spectral filter known in the art suitable for modifying the spectral content of a channel beam 108. For example, the tunable filter 112 may include, but is not required to include, a thin film spectral filter formed from one or more stacked layers. Further, the tunable filter 112 may include reflective spectral filters or transmissive spectral filters. In addition, a spectral filter may be formed from a single optical element or a combination of optical elements.

In another embodiment, the tunable filter 112 includes one or more tunable spectral filters in the optical path of at least one channel beam 108. In this regard, the spectral transmissivity of the filter (e.g. one or more cutoff wavelengths, one or more transmissivity values, or the like) may be adjusted by controlling the incident angle and/or the incident position of a channel beam 108. In another embodiment, the tunable filter 112 includes one or more discrete (e.g. non-tunable) spectral filters in the optical path of at least one channel beam 108. In this regard, the spectral transmissivity of the filter (e.g. one or more cutoff wavelengths, one or more transmissivity values, or the like) may be substantially constant with respect to the incident angle and/or the incident position of a channel beam 108.

Figure 3A:
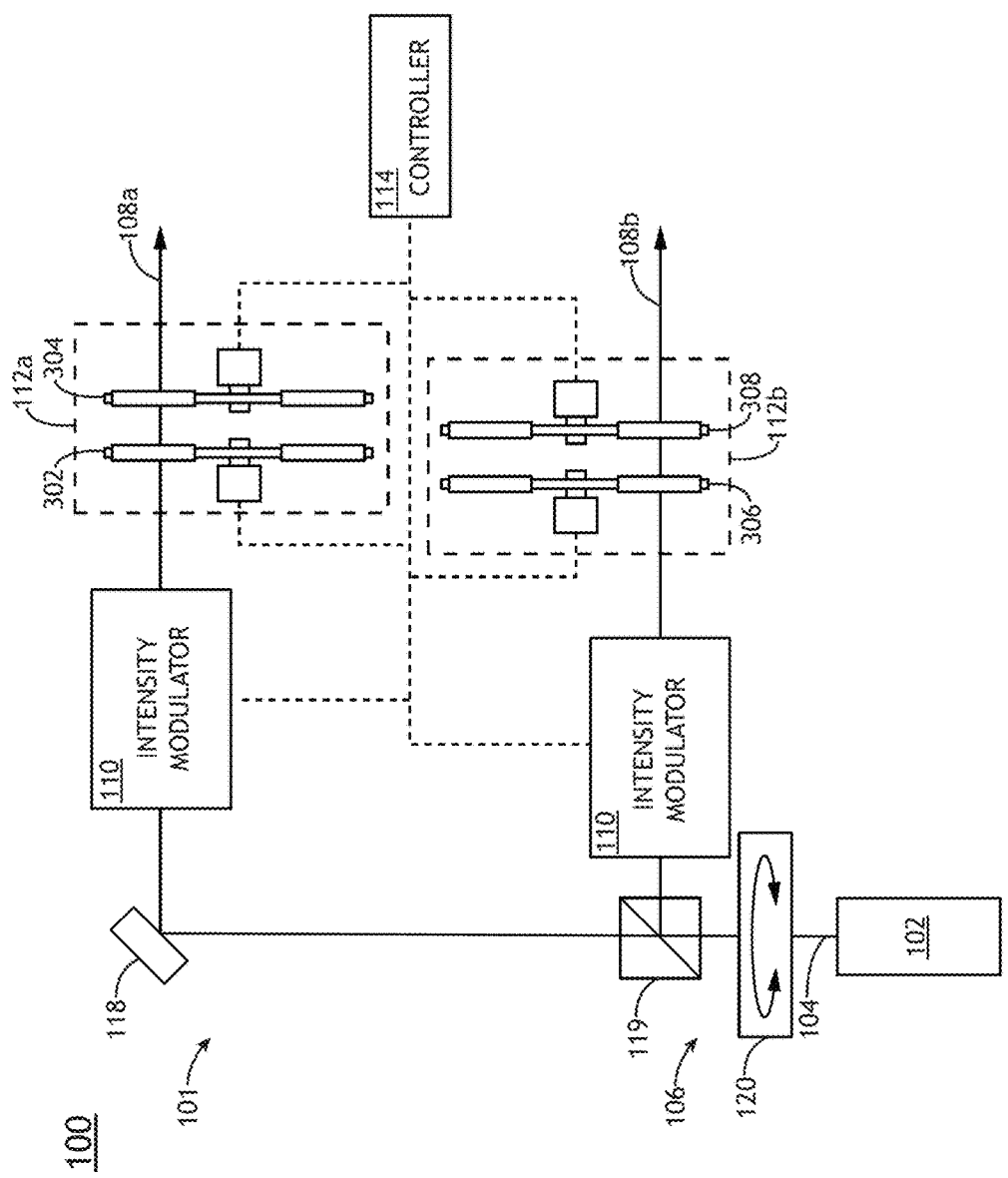
FIG. 3A is a conceptual view of a multi-channel illumination source illustrating a tunable filter including filter changers, in accordance with one or more embodiments of the present disclosure.

FIG. 3A is a conceptual view of a multi-channel tunable spectral filter 101 illustrating a tunable filter 112 including spectral filters secured in filter changers, in accordance with one or more embodiments of the present disclosure. In one embodiment, a first tunable filter 112*a* may include a first filter changer 302 and a second filter changer 304 to secure spectral filters to modify the spectral properties of a first channel beam 108*a*. In another embodiment, a second tunable filter 112*b* may include a third filter changer 306 and a fourth filter changer 308 to secure spectral filters to modify the spectral properties of a second channel beam 108*b*. In this regard, the spectrum of each channel beam 108*a,b* may be adjusted by selectively controlling the number and spectral transmissivity of the spectral filters within the filter changers placed in the path of the channel beams 108*a,b*. In one embodiment, the filter changers (e.g. filter changers 302-308) are adjustable such that one or more spectral filters may be selectively placed in the paths of each channel beam 108*a,b*. Further, the filter changers 302-308 may secure any type of spectral filter such as, but not limited to, a low-pass filter, a high-pass filter, a band-pass filter, or a band-reject filter.

It is recognized herein that cascading two or more spectral filters (e.g. located within filter changers, or the like) may provide superior performance relative to a single spectral filter. For example, a tunable filter 112 (e.g. tunable filter 112*a,b* as illustrated in FIG. 3A) including cascaded spectral filters having overlapping pass bands may exhibit a higher suppression ratio (e.g. a ratio of a transmittance of blocked wavelengths to a transmittance of passed wavelengths, or the like) than any of the constituent spectral filters individually. In this regard, the performance criteria of any particular spectral filter may be relaxed, while maintaining a desired level of suppression of wavelengths outside of a desired passband.

For example, it may be the case that the fabrication demands (e.g. complexity of fabrication, number of coatings, cost of fabrication, or the like) associated with a spectral filter may depend on multiple factors such as, but not limited to, the required suppression ratio, the range of wavelengths over which a required suppression ratio must be valid, or the steepness of a transition between passed wavelengths and blocked wavelengths. For example, the fabrication demands of a wideband band-pass filter may be less stringent than the fabrication demands of a narrowband band-pass filter. By way of another example, the fabrication demands of a filter in which a desired suppression ratio must be held for a large range of wavelengths outside the passband may be more stringent than the fabrication demands of a filter in which a desired suppression ratio must be held for a narrow range of wavelengths outside the passband.

FIGS. 3B through 3D are diagrams illustrating the spectral transmissivity of a tunable filter including two cascaded spectral filters. FIG. 3B is a diagram 310 illustrating the spectral transmissivity of a first spectral filter (e.g. mounted in the first filter changer 302, the third filter changer 306, or the like), in accordance with one or more embodiments of the present disclosure. In one embodiment, the first spectral filter includes a wide-band band-pass filter to pass wavelengths between a first wideband cutoff wavelength 312 and a second wideband cutoff wavelength 314 (e.g. defining a passband of wavelengths passed by the first spectral filter). Further, the first spectral filter may pass wavelengths within the passband with a first wideband transmissivity 316 and may pass wavelengths outside of the passband with a second wideband transmissivity 318. In this regard, a suppression ratio of the first spectral filter may correspond to a ratio of the second wideband transmissivity 318 to the first wideband transmissivity 316. In another embodiment, the first spectral filter provides a relatively high suppression ratio over a large range of wavelengths outside the passband.

FIG. 3C is a diagram 320 illustrating the spectral transmissivity of a second spectral filter (e.g. mounted in the second filter changer 304, the fourth filter changer 308, or the like), in accordance with one or more embodiments of the present disclosure. In another embodiment, the second spectral filter includes a narrow-band band-pass filter to pass wavelengths between a first narrow-band cutoff wavelength 322 and a second narrow-band cutoff wavelength 324 (e.g. defining a passband of wavelengths passed by the second spectral filter). Further, the second spectral filter may pass wavelengths within the passband with a first narrowband transmissivity 326 and may pass wavelengths outside of the passband with a second narrowband transmissivity 328. In this regard, a suppression ratio of the second spectral filter may correspond to a ratio of the second wideband transmissivity 318 to the first wideband transmissivity 316.

FIG. 3D is a diagram 330 illustrating the spectral transmissivity of the first spectral filter cascaded with the second spectral filter (e.g. as illustrated in FIG. 3A), in accordance with one or more embodiments of the present disclosure. For example, the cascaded spectral filters may pass wavelengths within a passband defined by the first narrowband transmissivity 326 and the second narrow-band cutoff wavelength 324. Further, the transmissivity 332 of the cascaded spectral filters may be a combination (e.g. a multiplicative combination) of the first wideband transmissivity 316 and the first narrowband transmissivity 326. In one embodiment, the tunable filter 112 may have a high suppression ratio over a relatively large range of wavelengths. Further, as illustrated in FIGS. 3B and 3C, it may be the case that a desired performance of the tunable filter 112 may be achieved using the cascaded first and second spectral filters in such a way that the fabrication demands on each of the first and second spectral filters are reduced relative to a tunable filter 112 having a single spectral filter with the same performance characteristics. For example, as illustrated in FIGS. 3B and 3C, the first spectral filter may exhibit a high suppression ratio over a large range of wavelengths outside of the passband, but may exhibit a wide passband. Further, the second spectral filter may exhibit a narrow passband, but may exhibit a lower suppression ratio for wavelengths outside of the passband of the first spectral filter.

Figure 4:
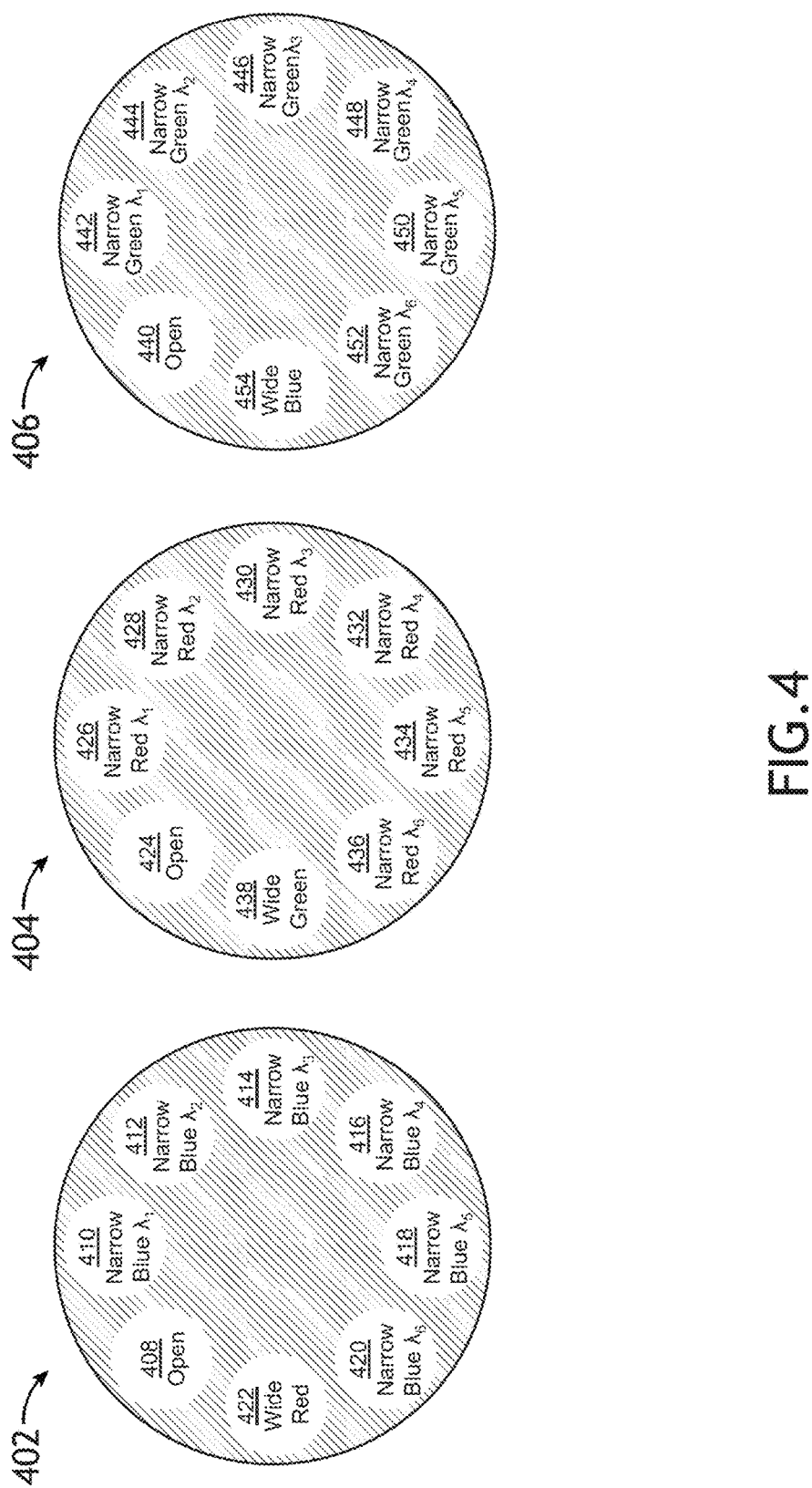
FIG. 4 is a schematic diagram of three filter changers containing spectral filters suitable for spectrally filtering a channel beam to include a narrow-band spectral profile that is tunable within three spectral windows, in accordance with one or more embodiments of the present disclosure.

FIG. 4 is a schematic diagram of three filter changers containing spectral filters suitable for spectrally filtering a channel beam 108 to include a narrow-band spectral profile that is tunable within three spectral windows, in accordance with one or more embodiments of the present disclosure. In one embodiment, a tunable filter 112 having three filter changers with eight filter mounts each provides narrowband spectral filtering of a channel beam 108 with eighteen selectable center wavelengths.

In another embodiment, the tunable filter 112 includes a first filter changer 402, a second filter changer 404, and a third filter changer 406. In another embodiment, each filter changer 402-406 includes eight filter mounts suitable for securing a spectral filter. For example, the first filter changer 402 may include filter mounts 408-422, the second filter changer 404 may include filter mounts 424-438, and the third filter changer 406 may include filter mounts 440-454.

In another embodiment, each filter changer includes an open mount in which no filter is mounted. In this regard, a channel beam 108 may selectively pass through each filter changer without spectral modification. For example, filter mounts 408, 424, and 440 may be open mounts.

In another embodiment, the tunable filter 112 provides narrowband spectral filtering using a wideband band-pass filter cascaded with a narrowband band-pass filter (e.g. as illustrated in FIGS. 3B through 3D). For example, filter mount 422 may include a wideband band-pass filter having a first passband (e.g. a red passband), filter mount 438 may include a wideband band-pass filter having a second passband (e.g. a green passband, and filter mount 454 may include a wideband band-pass filter having a third passband (e.g. a blue passband). Further, filter mounts 426-436 may include narrowband band-pass filters with center wavelengths within the first passband. In this regard, a channel beam 108 may be tuned to a wavelength within the first passband by setting the first filter changer 402 to filter mount 422, the second filter changer 404 to any of filter mounts 426-436, and the third filter changer 406 to filter mount 408 (e.g. open). Filter mounts 442-452 may include narrowband band-pass filters with center wavelengths within the second passband. In this regard, a channel beam 108 may be tuned to a wavelength within the second passband by setting the first filter changer 402 to filter mount 408 (e.g. open), the second filter changer 404 to 438, and the third filter changer 406 to any of filter mounts 442-452. Filter mounts 410-420 may include narrowband band-pass filters with center wavelengths within the third passband. In this regard, a channel beam 108 may be tuned to a wavelength within the third passband by setting the first filter changer 402 to any of filter mounts 410-420, the second filter changer 404 to 424 (e.g. open), and the third filter changer 406 to filter mount 454.

It is to be understood that the descriptions of red, green, and blue passbands are provided solely for illustrative purposes and should not be interpreted as limiting. In a general sense, the tunable filter 112 may include band-pass filters in any region of the spectrum including, but not limited to, ultraviolet wavelengths, visible wavelengths, or infrared wavelengths.

Figure 5:
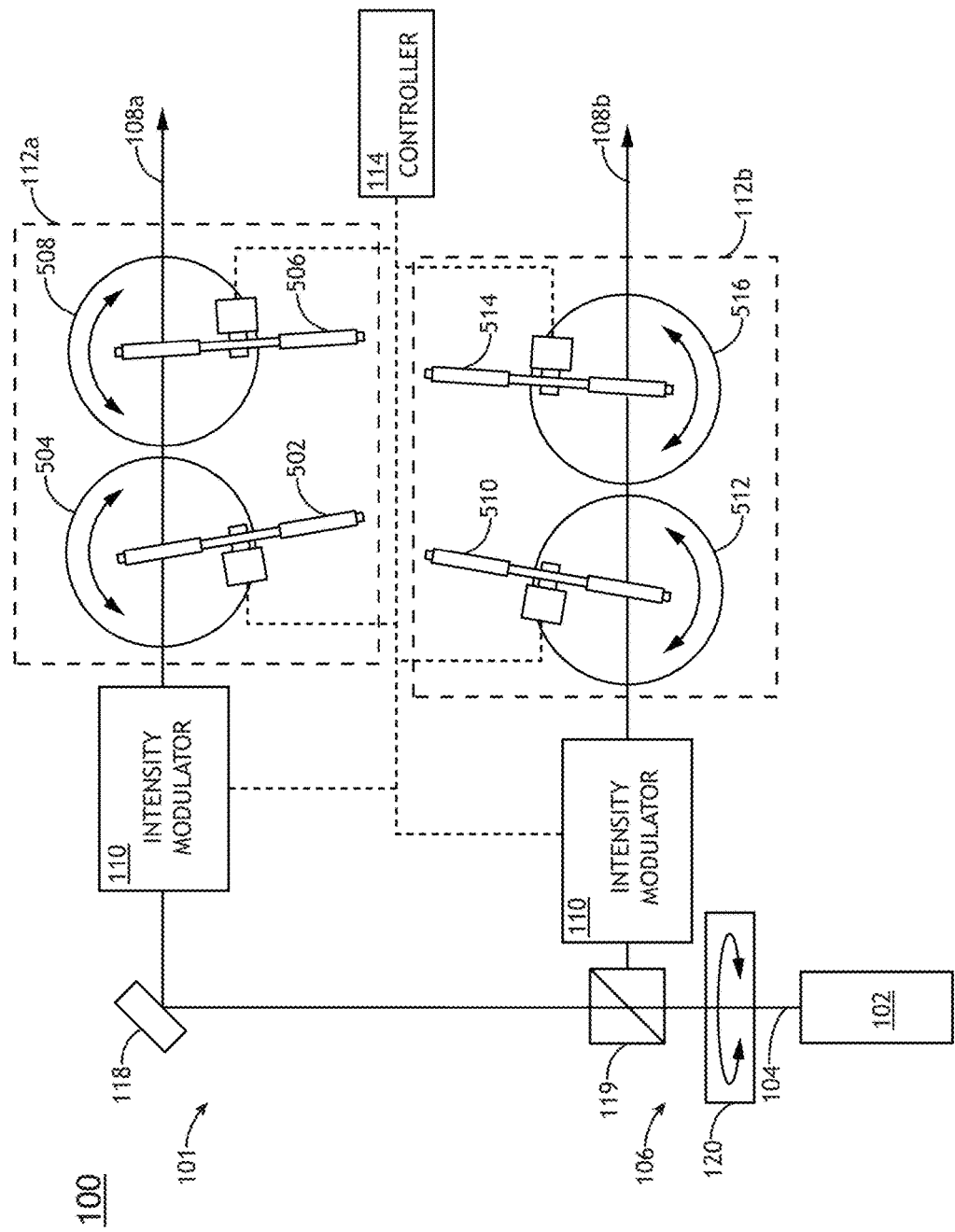
FIG. 5 is a conceptual view of a multi-channel illumination source illustrating a tunable filter including angularly-tunable spectral filters, in accordance with one or more embodiments of the present disclosure.

In another embodiment, a tunable filter 112 may include angularly-tunable spectral filters in which one or more filtering characteristics (e.g. a cutoff wavelength, a center wavelength, a transmissivity value, or the like) may be tuned according to the angle of incidence of a channel beam 108. Further, angularly-tunable spectral filters may include any type of spectral filter such as, but not limited to, a low-pass filter, a high-pass filter, a band-pass filter, or a band-reject filter. FIG. 5 is a conceptual view of a multi-channel tunable spectral filter 101 illustrating a tunable filter 112 including angularly-tunable spectral filters, in accordance with one or more embodiments of the present disclosure. For example, a filter mount (e.g. a single filter mount, a filter changer, or the like) may be secured on a rotational stage such that the angle of incidence of a channel beam 108 on a tunable spectral filter may be adjusted. In one embodiment, as illustrated in FIG. 5, a first tunable filter 112a may include a low-pass filter in a first filter mount 502 secured on a first rotation stage 504 and a high-pass filter in a second filter mount 506 secured on a second rotational stage 508. In another embodiment, a second tunable filter 112b may include a low-pass filter in a third filter mount 510 secured on a third rotation stage 512 and a high-pass filter in a fourth filter mount 514 secured on a fourth rotational stage 516.

Figure 6:
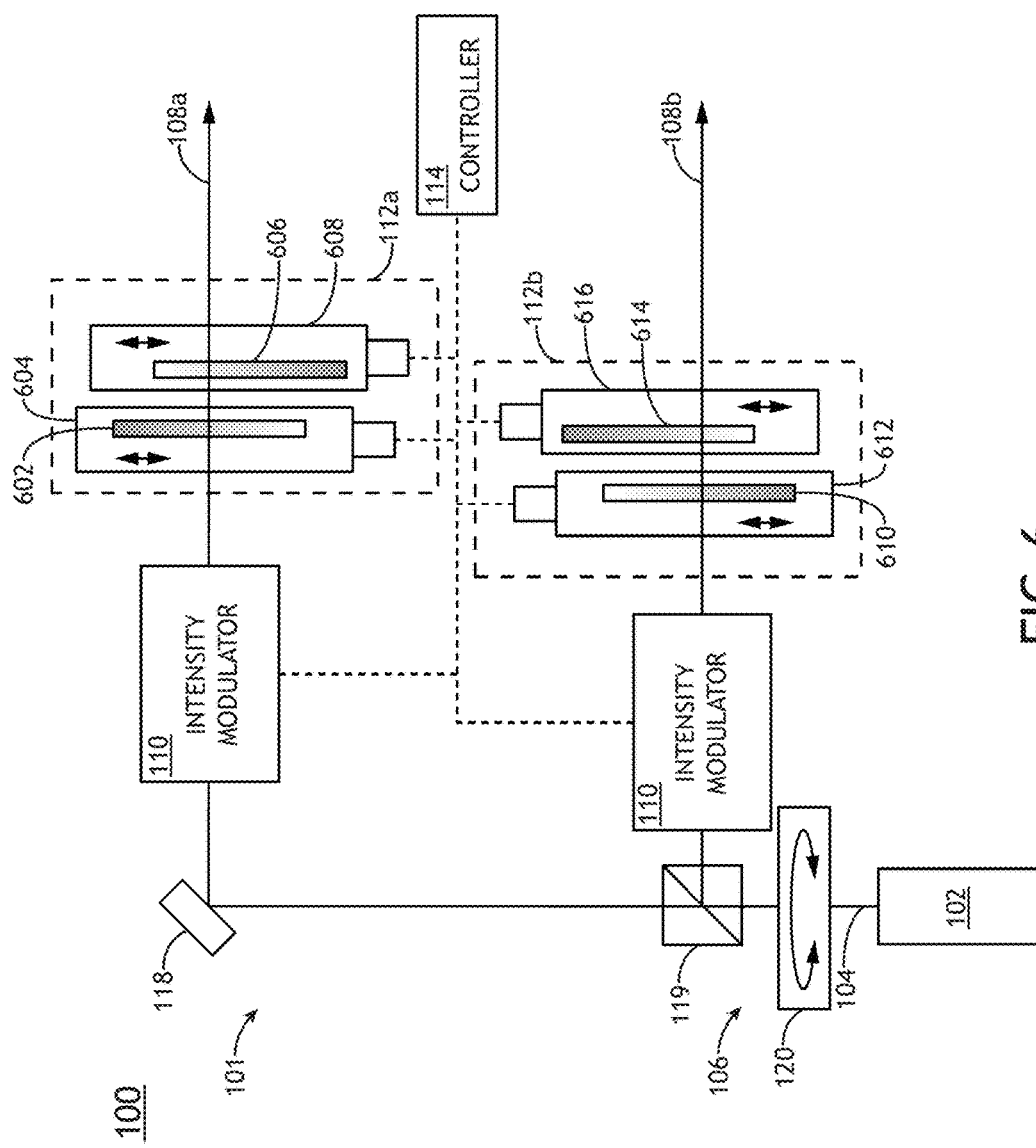
FIG. 6 is a conceptual view of a multi-channel illumination source illustrating a tunable filter including linearly-tunable spectral filters, in accordance with one or more embodiments of the present disclosure.

In another embodiment, a tunable filter 112 may include linearly-tunable spectral filters in which one or more filtering characteristics (e.g. a cutoff wavelength, a center wavelength, a transmissivity value or the like) may be tuned according to the linear position of a channel beam 108 on the filter. For example, a linearly-tunable spectral filter may include one or more thin films having a wedge profile such that a thickness may vary across the length of the filter. Further, linearly-tunable spectral filters may include any type of spectral filter such as, but not limited to, a low-pass filter, a high-pass filter, a band-pass filter, or a band-reject filter. FIG. 6 is a conceptual view of a multi-channel tunable spectral filter 101 illustrating a tunable filter 112 including linearly-tunable spectral filters, in accordance with one or more embodiments of the present disclosure. For example, a filter mount (e.g. a single filter mount, a filter changer, or the like) may be secured on a linear stage such that the linear position of a channel beam 108 on a tunable spectral filter may be adjusted. In one embodiment, as illustrated in FIG. 6, a first tunable filter 112a may include a low-pass filter in a first filter mount 602 secured on a first linear stage 604 and a high-pass filter in a second filter mount 606 secured on a second linear stage 608. In another embodiment, a second tunable filter 112b may include a low-pass filter in a third filter mount 610 secured on a third linear stage 612 and a high-pass filter in a fourth filter mount 614 secured on a fourth linear stage 616.

Figure 7:
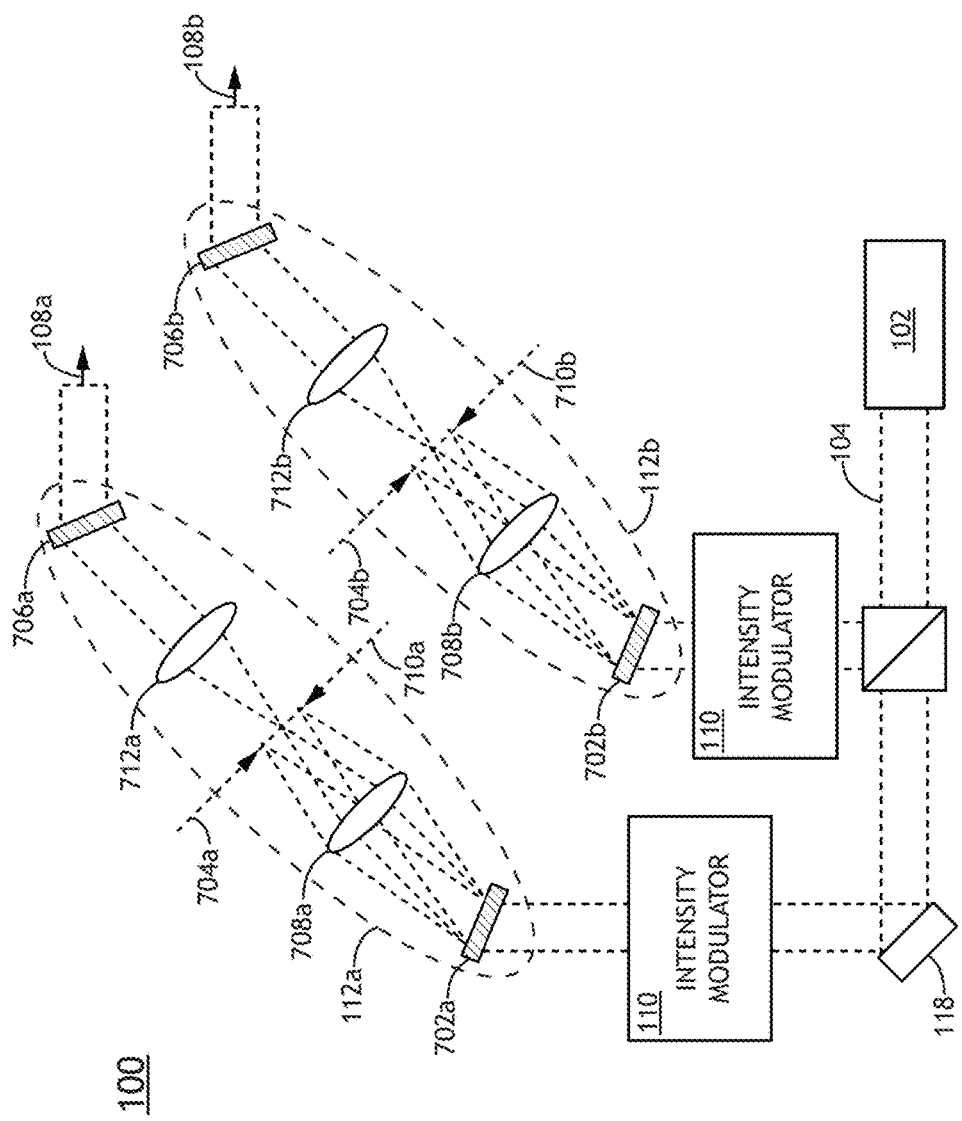
FIG. 7 is a conceptual view of a tunable filter including a double-grating monochromator with a spatial filter, in accordance with one or more embodiments of the present disclosure.

FIG. 7 is a conceptual view of a tunable filter 112 including a double-grating monochromator with a spatial filter, in accordance with one or more embodiments of the present disclosure. In another embodiment, a tunable filter 112a,b includes a first dispersive element 702a,b to spectrally disperse a channel beam (e.g. channel beam 108a or channel beam 108b), a filtering element 704a,b to operate as a spatial filter, and a second dispersive element 706a,b to spectrally recombine the channel beam to form a spectrally-filtered channel beam. In this regard, the second dispersive element 706a,b may remove the dispersion introduced by the first dispersive element 702a,b. Further, a spectral transmittance of the tunable filter 112a,b may be related to a spatial transmittance of the filtering element 704a,b.

The first dispersive element 702a,b may be any type of dispersive element known in the art suitable for introducing spectral dispersion into the channel beam (e.g. channel beam 108a or channel beam 108b). For example, the first dispersive element 702a,b may introduce dispersion into the channel beam through any mechanism such as, but not limited to, diffraction or refraction. Further, the first dispersive element 702a,b may be formed from transmissive and/or reflective optical elements.

In another embodiment, the first dispersive element 702a,b includes a dynamically-generated diffraction grating. In this regard, a diffraction grating may be dynamically generated in a substrate material (e.g. a transparent optical material). Further, the dispersive characteristics of the first dispersive element 702a,b may be dynamically modified in order to tune the multi-channel tunable spectral filter 101 by adjusting the physical characteristics of the dynamically-generated diffraction grating. For example, the period or the modulation depth of a dynamically-generated diffraction grating may be adjusted (e.g. via the controller 114) to control the value of dispersion (e.g. the angles at which particular wavelengths of illumination are diffracted). By way of another example, the modulation depth of the dynamically-generated diffraction grating may be adjusted (e.g. via the controller 114) to control the efficiency of dispersion (e.g. an efficiency value at which particular wavelengths of illumination is diffracted).

For example, the first dispersive element 702a,b may include, but is not limited to, an acousto-optic modulator on an electro-optic modulator. It is noted herein that a tunable filter 112 (e.g. tunable filter 112a,b) including a double grating monochromator with acousto-optical modulators may provide fast tuning of a spatially coherent channel beam (e.g. generated by a supercontinuum laser source, or the like). In one embodiment, the first dispersive element 702a,b includes an acousto-optic modulator consisting of a solid medium coupled with a transducer configured to generate ultrasonic waves that propagate through the solid medium. Properties of the solid medium such as, but not limited to, the refractive index may be modified by the propagating ultrasonic waves such that a channel beam is diffracted upon interaction with the solid medium. Furthermore, ultrasonic waves may propagate through the solid medium at the velocity of sound in the medium and have a wavelength related to the frequency of the drive signal as well as the velocity of sound in the solid medium. Accordingly, a modulation frequency and/or a modulation strength of a transducer may be dynamically adjusted to modify the physical characteristics of the dynamically-generated diffraction grating and the corresponding dispersive properties of the first dispersive element 702a,b.

In another embodiment, the tunable filter 112a,b includes a first optical element 708a,b (e.g. one or more lenses, or the like) to focus the spectrally-dispersed channel beam (e.g. channel beam 108a or channel beam 108b) to a focal plane 710a,b such that the spectrum of the channel beam may be spatially distributed across the focal plane 710a,b. Accordingly, the focal plane 710a,b may correspond to a diffraction plane of the multi-channel tunable spectral filter 101. In this regard, a "position" within the focal plane 710a,b may correspond to light from the channel beam exiting the first dispersive element 702a,b at a particular angle and thus a particular wavelength of illumination of the channel beam. For example, a first dispersive element 702a,b including a diffraction grating may diffract each wavelength of illumination of the channel beam at a different angle, whereupon each wavelength of illumination of the channel beam may be focused to a different location in the focal plane 710a,b.

In another embodiment, the filtering element 704a,b of the multi-channel tunable spectral filter 101 is located at the focal plane 710a,b. In this regard, the filtering element 704a,b may spatially filter the spectrally-dispersed channel beam (e.g. channel beam 108a or channel beam 108b). For example, the filtering element 704a,b may have a spatial transmittance describing the transmittance of illumination (e.g. illumination of any wavelength) as a function of position. Accordingly, the spectral power of each wavelength of illumination of the channel beam may be modified according to the spatial transmittance of the filtering element 704a,b. In this regard, the spectral transmittance of the multi-channel tunable spectral filter 101 may be controllable through the spatial transmittance of the filtering element 704a,b. In one instance, the filtering element 704a,b may pass a select wavelength (or wavelength range) of the channel beam.

The filtering element 704a,b may, but is not required to, have a shape corresponding to the shape of the focal plane 710a,b. In one embodiment, a filtering element 704a,b may have a curved shape to match a focal plane 710a,b including a curved surface (e.g. as determined by the first dispersive element 702a,b and/or the first optical element 708a,b).

In another embodiment, the multi-channel tunable spectral filter 101 includes a second optical element 712a,b (e.g. one or more lenses, or the like) to collect the spectrally-dispersed illumination passed by the filtering element 704a,b. For example, the second optical element 712a,b may collect at least a portion of the spectrally dispersed and filtered channel beam from the filtering element 704a,b. Further, the second optical element 712a,b may direct the collected spectrally dispersed and filtered illumination beam 104 to the second dispersive element 706a,b.

In another embodiment, the second dispersive element 706a,b spectrally combines the spectrally dispersed and filtered channel beam 108 to remove the spectral dispersion introduced by the first dispersive element 702a,b. In this regard, a channel beam (e.g. channel beam 108a or channel beam 108b) exiting the second dispersive element 706a,b may be a spectrally-filtered version of the input channel beam 108. For example, the dispersive characteristics of the second optical element 712a,b may be configured to counteract the dispersion induced by the first dispersive element 702a,b.

In another embodiment, the first optical element 708a,b and the second optical element 712a,b form an optical relay system. In this regard, the first optical element 708a,b and the second optical element 712a,b may generate an image of the distribution of the channel beam on the first dispersive element 702a,b at the second dispersive element 706a,b. Accordingly, the multi-channel tunable spectral filter 101 may minimally affect the properties of the channel beam such as, but not limited to, the divergence (e.g. degree of collimation), spatial coherence, or brightness (e.g. of the passed wavelengths), which may facilitate the integration of the multi-channel tunable spectral filter 101 into any system (e.g. a metrology system, or the like).

The filtering element 704a,b may have any spatial transmittance distribution in order to provide any filtering operation known in the art. Accordingly, the multi-channel tunable spectral filter 101 may operate as any type of spectral filter such as, but not limited to, a low-pass filter, a high-pass filter, a band-pass filter, or a notch-filter.

Figure 8:
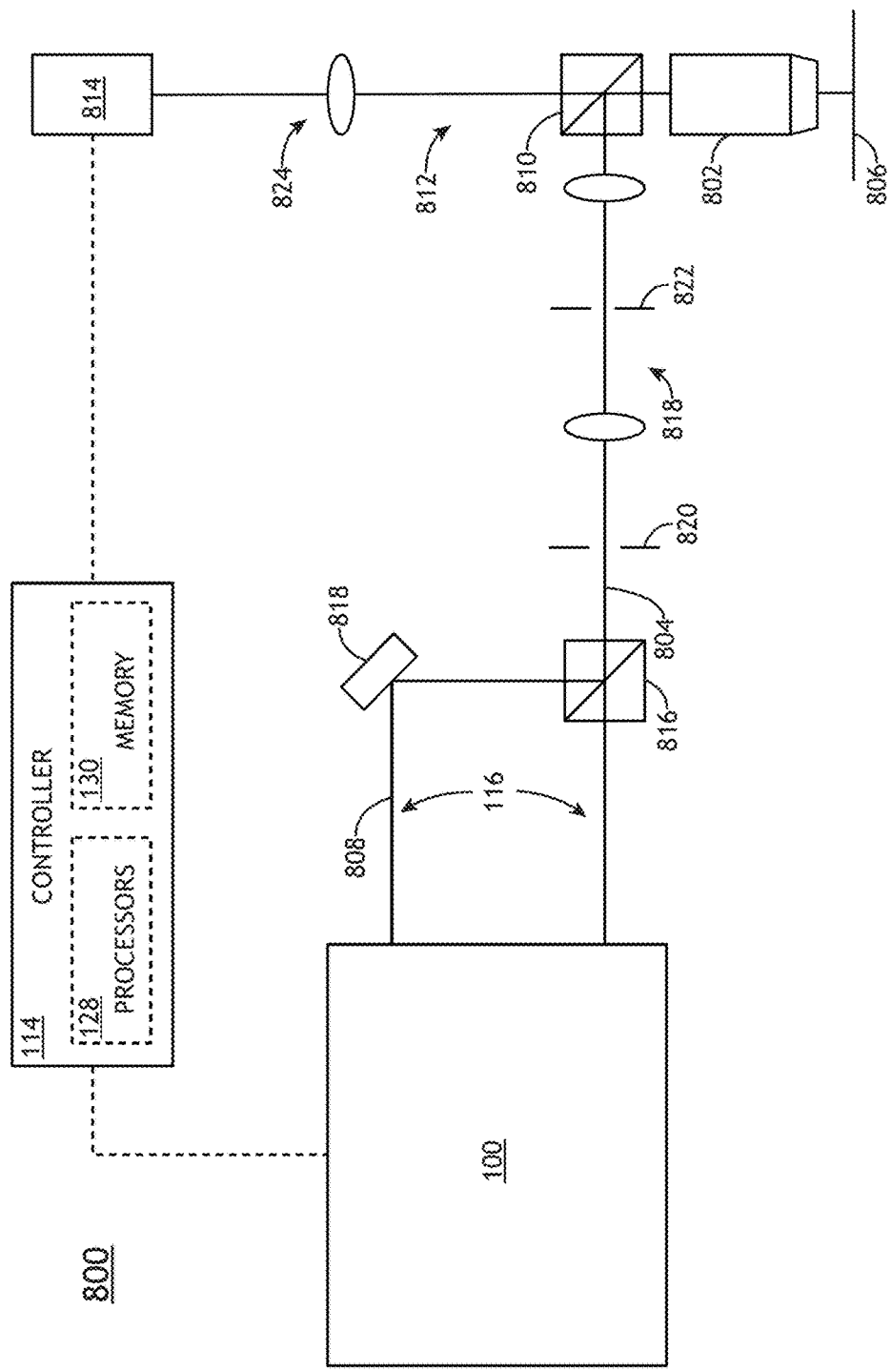
FIG. 8 is a conceptual view of a metrology system including a multi-channel illumination source, in accordance with one or more embodiments of the present disclosure.

The multi-channel tunable spectral filter 101 may be utilized as a part of an external optical system. FIG. 8 is a conceptual view of a metrology system 800 (e.g. a microscope, an imaging scatterometer, an angular resolved scatterometer, or the like) including a multi-channel illumination source 100, in accordance with one or more embodiments of the present disclosure. For example, a multi-channel illumination source 100 including a multi-channel tunable spectral filter 101 may provide a tunable illumination source for the metrology system 800.

In another embodiment, the metrology system 800 includes an objective lens 802 configured to direct the beam of illumination 804 to a sample 806 along an illumination pathway 808. In another embodiment, the metrology system 800 is configured in epi-mode with a beamsplitter 810 such that the objective lens 802 both directs the beam of illumination 804 to the sample 806 and collects illumination from the sample 806 at a normal angle. In another embodiment, the metrology system 800 includes one or more illumination optics along a collection pathway 812 to receive radiation emanating from the sample 806 (e.g. reflected, scattered, and/or diffracted portions of the illumination beam 804, radiation emitted by the sample 806, or the like) and direct the collected radiation to a detector 814.

In another embodiment, the beam of illumination 804 of the metrology system 800 includes any number of tunable illumination beams provided by the multi-channel tunable spectral filter 101. For example, the beam of illumination 804 may include any number of output illumination beams 116 from the multi-channel tunable spectral filter 101 (e.g. channel beams 108, combined output illumination beams 116, or the like). Further, each output illumination beam 116 provided by the multi-channel tunable spectral filter 101 may have selectively adjustable properties such as, but not limited to, spectral content, intensity, or polarization.

In another embodiment, the metrology system 800 may utilize tunable output illumination beams 116 provided by the multi-channel tunable spectral filter 101 to illuminate the sample 806. For example, the metrology system 800 may direct the tunable output illumination beams 116 to multiple portions of the sample 806 (e.g. multiple cells of a metrology target, or the like). Further, the metrology system 800 may direct the tunable output illumination beams 116 to the sample 806 simultaneously or sequentially. It is noted herein that the multi-channel tunable spectral filter 101 may efficiently tune the output illumination beams 116 (e.g. modify the spectral content of the output illumination beams 116) for efficient measurements. For example, a multi-channel tunable spectral filter 101 including a double grating monochromator formed from acousto-optical modulators may efficiently tune a spatially coherent broadband source such as, but not limited to, a supercontinuum laser source.

In another embodiment, as illustrated in FIG. 8, the metrology system 800 includes multi-channel tunable spectral filter 101 to produce two independently tunable channel beams 108 as output illumination beams 116. In another embodiment, the metrology system 800 includes a beam combiner 816 to combine the output illumination beams 116 into a single beam of illumination 804. In another embodiment, the illumination pathway 808 of the metrology system 800 includes a set of illumination optical elements 818 to direct the beam of illumination 804 to the sample 806. For example, the set of illumination optical elements 818 may include an optical relay to relay an illumination pupil 820 to the objective lens 802. In this regard, the objective lens 802 may illuminate the sample 806 with any distribution of illumination from the beam of illumination 804 including, but not limited to, critical illumination or köhler illumination. In another embodiment, the illumination pathway 808 may include an illumination field stop 822 to adjust the spatial extent of the beam of illumination 804 in a field plane.

In another embodiment, the collection pathway 812 includes a set of collection optical elements 824 to direct illumination from the sample 806 to the detector. For example, the set of collection optical elements 824 may include an optical relay to relay a desired distribution of illumination from the objective lens 802 to the detector 814. In one instance, the set of collection optical elements 824 may relay an image of the sample 806 to the detector 814. In another instance, the set of collection optical elements 824 may relay an image of a pupil plane (e.g. a back focal plane of the objective lens 802) to the detector 814. Accordingly, the metrology system 800 may detect the angular distribution of radiation from the sample 806.

Figure 9:
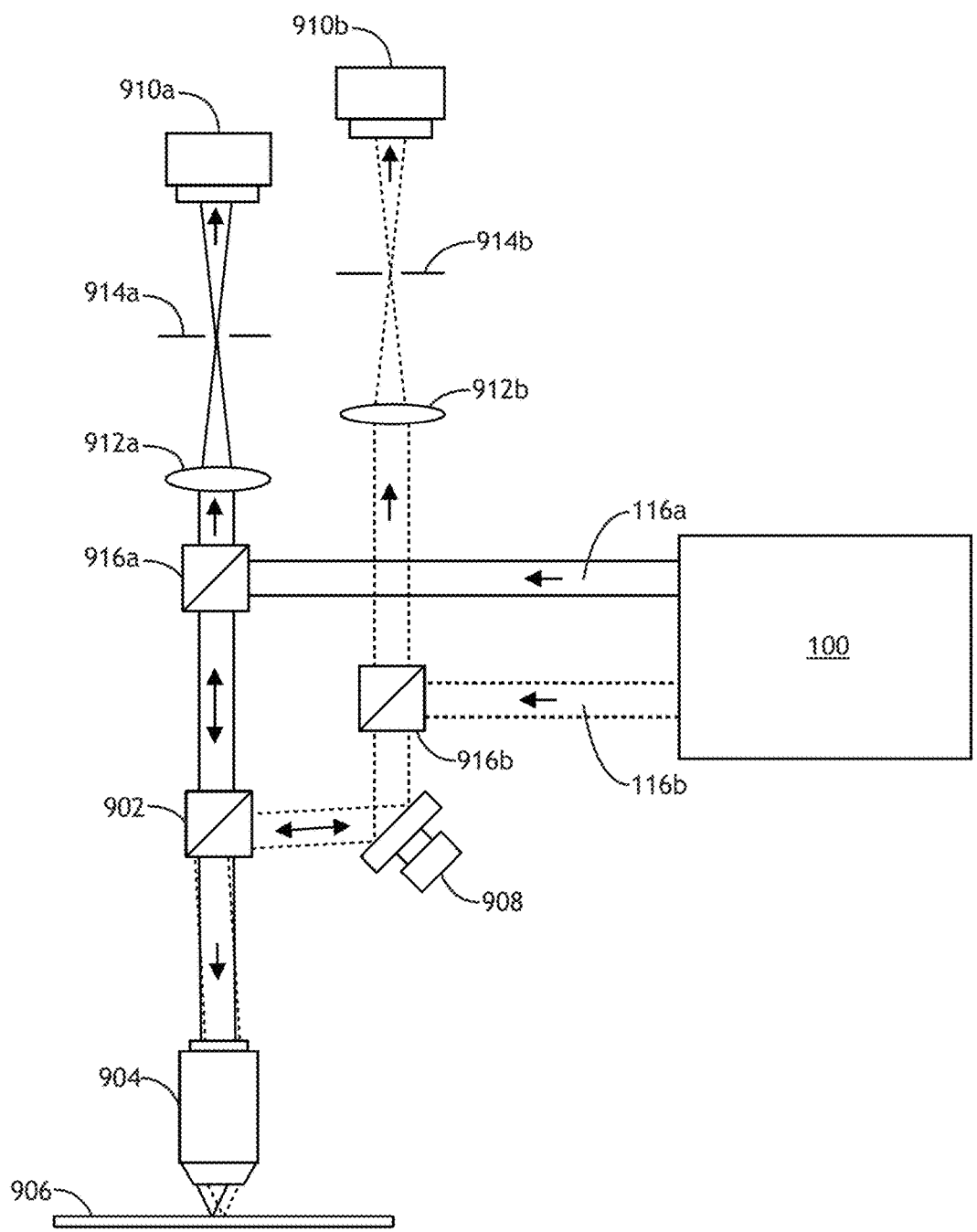
FIG. 9 is a conceptual view of a multi-beam metrology system including a multi-channel illumination source with a multi-channel tunable spectral filter, in accordance with one or more embodiments of the present disclosure.

FIG. 9 is a conceptual view of a multi-beam metrology system 900 including a multi-channel illumination source 100 with a multi-channel tunable spectral filter 101, in accordance with one or more embodiments of the present disclosure. In one embodiment, a multi-channel illumination source 100 provides two output illumination beams 116a,b having different spectra. In one embodiment, the metrology system 900 includes a beam combiner 902 to collect the output illumination beams 116a,b to a single optical column. For example, as illustrated in FIG. 9, the beam combiner 902 may include a beamsplitter. Further, beam combiner 902 may direct the output illumination beams 116 to a single objective lens 904. In this regard, the two output illumination beams 116 provided by the multi-channel illumination source 100 may be directed to a sample 906.

In one embodiment, the two output illumination beams 116a,b may be directed to the same position on the sample 906. In another embodiment, the two output illumination beams 116a,b may be directed to different positions on the sample 906. For example, as illustrated in FIG. 9, the metrology system 900 may include a beam scanner 908 to deflect one output illumination beam with respect to the other (e.g. output illumination beam 116b with respect to output illumination beam 116a) such that the two output illumination beams 116a,b may be directed to different positions of the sample 906 within the field of view of the objective lens 904. The beam scanner 908 may be any element known in the art suitable for deflecting one output illumination beam with respect to the other such as, but not limited to, a reflective element with adjustable tip, tilt, and/or position (e.g. mounted on an adjustable actuator controlled by the controller 114, or the like) or a galvanometric mirror. In one instance, the metrology system 900 may include a scatterometry-based overlay metrology system in which the two output illumination beams 116a,b may be directed to two scatterometry metrology targets for simultaneous measurement.

In another embodiment, the metrology system 900 includes two detectors 910a,b positioned to capture radiation emanating from the sample 906 from the two positions illuminated by the output illumination beams 116a,b. For example, the objective lens 904 may simultaneously direct illumination to the sample 906 and collect radiation emanating from the sample 906. In one instance, as illustrated in FIG. 9, the metrology system 900 may be configured to capture pupil images associated with radiation emanating from the sample 906 (e.g. associated with the angular distribution of radiation from the sample 906). In this regard, the metrology system 900 may include one or more optical elements 912a,b to relay a pupil plane (e.g. a back focal plane of the objective lens 904 to the detectors 910a,b. Further, the metrology system 900 may include additional elements (e.g. spatial filters 914a,b, or the like) to condition the illumination collected by the objective lens 904. In another instance, the metrology system 900 may be configured to capture images of the sample 906 (e.g. a surface of the sample 906). In another embodiment, the metrology system 900 may include one or more beamsplitters 916a,b to facilitate the simultaneous illumination of and detection of radiation from the sample 906.

Referring generally to FIGS. 8 and 9, the one or more detectors (e.g. detector 814, detectors 910a,b, or the like) may include any detector known in the art. For example, a detector may include, but are not limited to, a CCD detector, a photodiode, an avalanche photodiode (APD) and/or or a photomultiplier tube (PMT). It is further noted that a detector may be a multi-channel detector configured to simultaneously detect signals from multiple detection regions on a sample.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A metrology system, comprising:
    an illumination source configured to generate an illumination beam having an input spectrum;
    a multi-channel spectral filter, comprising:
        two or more filtering channels having two or more spectral transmissivity distributions, wherein at least one of the two or more filtering channels includes a spectral filter; and
        a channel selector including at least one of an optical modulator or a polarization rotator configured to switch selected intensity fractions of the illumination beam into one or more selected filtering channels of the two or more filtering channels without modifying the input spectrum of the illumination beam, wherein the selected intensity fractions of the illumination beam directed to the one or more selected filtering channels have the same input spectrum as the illumination beam to provide independent filtering of the input spectrum by the one or more selected filtering channels, wherein the one or more selected filtering channels generate one or more filtered output beams based on the spectral transmissivity distributions of the one or more selected filtering channels;
    at least one beam combiner to combine illumination from the two or more filtering channels to a single optical column;
    a single focusing element to direct illumination from the two or more filtering channels in the single optical column to a sample;

at least one adjustable beam deflector to selectively adjust an optical path of illumination from at least one filtering channel of the two or more filtering channels through the single focusing element to illuminate the sample at two or more selected locations; and two or more detectors to capture radiation from the two or more selected locations of the sample.

2. The metrology system of claim 1, wherein the illumination source comprises:
a spatially coherent illumination source.

3. The metrology system of claim 2, wherein the spatially coherent illumination source comprises:
a supercontinuum laser.

4. The metrology system of claim 1, wherein the illumination source comprises:
at least one of an arc lamp, a discharge lamp, an electrodeless lamp, or a laser-sustained plasma source.

5. The metrology system of claim 1, wherein the channel selector comprises:
at least one of a beamsplitter.

6. The metrology system of claim 1, wherein the channel selector comprises:
at least one of a waveplate or an electro-optic cell; and
a polarizing beamsplitter.

7. The metrology system of claim 1, wherein the channel selector includes an optical modulator comprising:
at least one of an acousto-optic modulator, an electro-optic modulator, a galvanometer mirror, or a piezoelectric mirror.

8. The metrology system of claim 1, wherein the spectral filter of at least one of the two or more filtering channels includes one or more tunable spectral filters.

9. The metrology system of claim 8, wherein the one or more tunable spectral filters comprise:
at least one of a low-pass filter, a high-pass filter, a band-pass filter, or a band-reject filter.

10. The metrology system of claim 8, wherein the one or more tunable spectral filters comprise:
one or more filter changers to secure one or more selectable discrete spectral filters.

11. The metrology system of claim 8, wherein one or more filtering characteristics of the one or more tunable spectral filters are tunable based on at least one of an incident angle or an incident position of the selected intensity fraction of the illumination beam.

12. The metrology system of claim 11, wherein the one or more filtering characteristics comprise:
at least one of a spectral bandwidth, a center wavelength, or a transmissivity value.

13. The metrology system of claim 8, further comprising:
one or more translatable filter mounts to secure the one or more tunable spectral filters.

14. The metrology system of claim 13, wherein at least one of the one or more translatable filter mounts comprises:
a linearly translatable filter mount configured to adjust an incident position of the selected intensity fraction of the illumination beam on the one or more tunable filters.

15. The metrology system of claim 13, wherein at least one of the one or more translatable filter mounts comprises:
a rotationally translatable filter mount configured to adjust an incident angle of the selected intensity fraction of the illumination beam on the one or more tunable filters.

16. The metrology system of claim 8, wherein a tunable filter of the one or more tunable filters comprises:
a double grating monochromator.

17. The metrology system of claim 16, wherein the double grating monochromator comprises:
a first grating configured to spectrally disperse the selected intensity fraction of the illumination beam as a spatially-dispersed channel beam, wherein a dispersion of the first grating is configurable;
a first optical lens, the first optical lens configured to focus the spectrally-dispersed channel beam at a focal plane, wherein a distribution of a spectrum of the spectrally-dispersed channel beam at the focal plane is determined by the dispersion of the first grating;
a spatial filter located at the focal plane, wherein the spatial filter spatially filters the spectrum of the spectrally-dispersed channel beam;
a second optical lens configured to collect the spectrally-dispersed channel beam transmitted from the spatial filter; and
a second grating configured to remove the dispersion of the spectrally-dispersed channel beam.

18. The metrology system of claim 1, wherein at least one filtering channel of the two or more filtering channels includes an intensity modulator.

19. The metrology system of claim 18, wherein the intensity modulator comprises:
at least one of a shutter or a neutral density filter.

20. The metrology system of claim 18, wherein the intensity modulator comprises:
at least one of a waveplate or an electro-optic cell; and
a polarizer.

21. A multi-channel illumination source, comprising:
an illumination source configured to generate an illumination beam having an input spectrum; and
a multi-channel spectral filter comprising:
two or more filtering channels having two or more spectral transmissivity distributions, wherein at least one of the two or more filtering channels includes a spectral filter; and
a channel selector including at least one of an optical modulator or a polarization rotator configured to dynamically direct selected intensity fractions of the illumination beam into one or more selected filtering channels of the two or more filtering channels without modifying the input spectrum of the illumination beam, wherein the selected intensity fractions of the illumination beam directed to the one or more selected filtering channels have the same input spectrum as the illumination beam to provide independent filtering of the input spectrum by the one or more selected filtering channels, wherein the one or more selected filtering channels generate one or more filtered output beams based on the spectral transmissivity distributions of the one or more selected filtering channels and the input spectrum.

22. The multi-channel illumination source of claim 21, wherein the illumination source comprises:
a single illumination source.

23. The multi-channel illumination source of claim 21, wherein the illumination source comprises:
a spatially coherent illumination source.

24. The multi-channel illumination source of claim 23, wherein the spatially coherent illumination source comprises:
a supercontinuum laser.

25. The multi-channel illumination source of claim 21, wherein the illumination source comprises:
at least one of an arc lamp, a discharge lamp, an electrodeless lamp, or a laser-sustained plasma source.

26. The multi-channel illumination source of claim 21, further comprising:
  at least one beam combiner configured to combine illumination from the two or more filtering channels to a common output beam path to generate a combined filtered output beam.

27. The multi-channel illumination source of claim 21, wherein the one or more selected filtering channels comprise:
  a single selected filtering channel at a given time, wherein the channel selector is configured to direct the illumination beam to the single selected filtering channel of the two or more filtering channels.

28. The multi-channel illumination source of claim 21, wherein the one or more selected filtering channels comprise:
  two or more simultaneously selected filtering channels, wherein the channel selector is configured to simultaneously direct selected intensity fractions of the illumination beam to the two or more simultaneously selected filtering channels to generate at least two filtered output beams.

29. The multi-channel illumination source of claim 21, wherein the channel selector comprises:
  at least one of a waveplate or an electro-optic cell; and
  a polarizing beamsplitter.

30. The multi-channel illumination source of claim 21, wherein the channel selector includes an optical modulator comprising:
  at least one of an acousto-optic modulator, an electro-optic modulator, a galvanometer mirror, or a piezoelectric mirror.

31. The multi-channel illumination source of claim 21, wherein at least one filtering channel of the two or more filtering channels includes one or more tunable spectral filters.

32. The multi-channel illumination source of claim 31, wherein the one or more tunable spectral filters comprise:
  at least one of a low-pass filter, a high-pass filter, a band-pass filter, or a band-reject filter.

33. The multi-channel illumination source of claim 31, wherein the one or more tunable spectral filters comprise:
  one or more filter changers to secure one or more selectable discrete spectral filters.

34. The multi-channel illumination source of claim 31, wherein one or more filtering characteristics of the one or more tunable spectral filters are tunable by based on at least one of an incident angle or an incident position of the selected intensity fraction of the illumination beam.

35. The multi-channel illumination source of claim 34, wherein the one or more filtering characteristics comprise:
  at least one of a spectral bandwidth, a center wavelength, or a transmissivity value.

36. The multi-channel illumination source of claim 31, further comprising:
  one or more translatable filter mounts to secure the one or more tunable spectral filters.

37. The multi-channel illumination source of claim 36, wherein at least one of the one or more translatable filter mounts comprises:
  a linearly translatable filter mount configured to adjust an incident position of the selected intensity fraction of the illumination beam on the one or more tunable filters.

38. The multi-channel illumination source of claim 36, wherein at least one of the one or more translatable filter mounts comprises:
  a rotationally translatable filter mount configured to adjust an incident angle of the selected intensity fraction of the illumination beam on the one or more tunable filters.

39. The multi-channel illumination source of claim 31, wherein a tunable filter of the one or more tunable filters comprises:
  a double grating monochromator.

40. The multi-channel illumination source of claim 36, wherein the double grating monochromator comprises:
  a first grating configured to spectrally disperse the selected intensity fraction of the illumination beam as a spatially-dispersed channel beam, wherein a dispersion of the first grating is configurable;
  a first optical lens, the first optical lens configured to focus the spectrally-dispersed channel beam at a focal plane, wherein a distribution of a spectrum of the spectrally-dispersed channel beam at the focal plane is determined by the dispersion of the first grating;
  a spatial filter located at the focal plane, wherein the spatial filter spatially filters the spectrum of the spectrally-dispersed channel beam;
  a second optical lens configured to collect the spectrally-dispersed channel beam transmitted from the spatial filter; and
  a second grating configured to remove the dispersion of the spectrally-dispersed channel beam.

41. The multi-channel illumination source of claim 21, wherein at least one filtering channel of the two or more filtering channels includes an intensity modulator.

42. The multi-channel illumination source of claim 41, wherein the intensity modulator comprises:
  at least one of a shutter or a neutral density filter.

43. The multi-channel illumination source of claim 41, wherein the intensity modulator comprises:
  at least one of a waveplate or an electro-optic cell; and
  a polarizer.

44. A multi-channel spectral filter, comprising:
  two or more filtering channels having two or more spectral distributions, wherein at least one of the two or more filtering channels includes a spectral filter; and
  a channel selector including at least one of an optical modulator or a polarization rotator configured to switch selected intensity fractions of an illumination beam having an input spectrum into one or more selected filtering channels of the two or more filtering channels without modifying the input spectrum of the illumination beam, wherein the selected intensity fractions of the illumination beam directed to the one or more selected filtering channels have the same input spectrum as the illumination beam to provide independent filtering of the input spectrum by the one or more selected filtering channels, wherein the one or more selected filtering channels generate one or more filtered output beams based on the spectral transmissivity distributions of the one or more selected filtering channels and the input spectrum.

45. The multichannel illumination source of claim 26, wherein at least one of the two or more filtering channels further include filtering-channel shutters to selectively pass the corresponding one or more filtered output beams.

46. The multichannel illumination source of claim 45, wherein the illumination beam is linearly polarized, wherein the channel selector comprises:
  at least one non-polarizing beamsplitter, wherein the at least one beam combiner comprises:

at least one additional non-polarizing beamsplitter, wherein the combined filtered beam is linearly polarized.

47. The multichannel illumination source of claim 46, wherein the multichannel illumination source further comprises:

at least one of a waveplate or an electro-optic cell configured to selectively adjust a direction of polarization of the combined filtered beam; and a polarizing beamsplitter to split the combined filtered beam into two output channels based on the direction of polarization of the combined filtered beam, wherein portions of the combined filtered beam within the two output channels are linearly polarized along orthogonal polarization directions.

48. The multichannel illumination source of claim 21, wherein the illumination beam is linearly polarized, wherein the two or more filtering channels comprise:

a first filtering channel and a second filtering channel, wherein the channel selector is configured to divide the illumination beam between the two filtering channels.

49. The multichannel illumination source of claim 48, further comprising:

a first polarizing beamsplitter to split the first filtered beam into a first output channel and a second output channel based on the direction of polarization of the first filtered beam, wherein the first output channel and the second output channel are orthogonally polarized; and a second polarizing beamsplitter to split the second filtered beam into a third output channel and a fourth output channel based on the direction of polarization of the second filtered beam, wherein the third output channel and the fourth output channel are orthogonally polarized.

50. The multi-channel illumination source of claim 21, wherein the channel selector includes a polarization controller comprising:

at least one of a waveplate or an electro-optical cell.

* * * * *